United States Patent
Bammer et al.

(10) Patent No.: US 10,369,287 B2
(45) Date of Patent: *Aug. 6, 2019

(54) MEDICATION INJECTOR WITH CAPACITIVE FILL LEVEL MEASUREMENT CAPACITY, AND CONTACT SENSOR

(71) Applicants: SEIBERSDORF LABOR GMBH, Seibersdorf (AT); AIT AUSTRIAN INSTITUE OF TECHNOLOGY GMBH, Vienna (AT)

(72) Inventors: Manfred Bammer, Vienna (AT); Gernot Schmid, Bromberg (AT); Otmar Putz, Bromberg (AT)

(73) Assignees: Siebersdorf Labor GmbH, Seibersdorf (AT); AIT Austrian Institute of Technology GmbH, Vienna (AT)

( * ) Notice: Subject to any disclaimer, the term of this patent is extended or adjusted under 35 U.S.C. 154(b) by 86 days.

This patent is subject to a terminal disclaimer.

(21) Appl. No.: 15/302,044

(22) PCT Filed: Mar. 9, 2015

(86) PCT No.: PCT/AT2015/050061
§ 371 (c)(1),
(2) Date: Oct. 5, 2016

(87) PCT Pub. No.: WO2015/157785
PCT Pub. Date: Oct. 22, 2015

(65) Prior Publication Data
US 2017/0119970 A1 May 4, 2017

(30) Foreign Application Priority Data
Apr. 15, 2014 (AT) ............................... A50283/2014
Jul. 9, 2014 (AT) ............................... A50477/2014

(51) Int. Cl.
A61M 5/24 (2006.01)
G01F 23/26 (2006.01)
(Continued)

(52) U.S. Cl.
CPC ................ *A61M 5/24* (2013.01); *A61J 1/062* (2013.01); *A61J 1/065* (2013.01); *A61M 5/3134* (2013.01);
(Continued)

(58) Field of Classification Search
CPC ............ A61M 5/24; A61M 2005/3126; A61M 2205/3317; A61M 2205/3389;
(Continued)

(56) References Cited

U.S. PATENT DOCUMENTS 6,110,148 A     8/2000  Brown et al.
6,490,920 B1 *  12/2002 Netzer .................... G01C 9/06
                                                324/687
(Continued)

FOREIGN PATENT DOCUMENTS

DE      102004040441 A1    6/2006
WO      2006021295 A1      3/2006
(Continued)

*Primary Examiner* — Natalie Huls
*Assistant Examiner* — Monica S Young
(74) *Attorney, Agent, or Firm* — Laurence A. Greenberg; Werner H. Stemer; Ralph E. Locher

(57) ABSTRACT

A medication injector for dispensing liquid medications to people includes a container which is filled with the liquid and which has an opening at one end for dispensing the liquid and at least one pair of capacitive measuring electrodes disposed opposite each other in the outer region of the container, in particular on the wall, for determining the permittivity of the respective medium in the intermediate region between the measuring electrodes. The measuring electrodes are used by the injector to determine the fill level (Continued)

of the container. A shielding surrounds the measuring electrodes in the manner of a sheath, is disposed around the container, and reduces possible external interfering influences on the capacitive measurement, such as those resulting from contact, for example. Additionally, a contact sensor is provided which can indicate the measurement as invalid.

20 Claims, 17 Drawing Sheets

(51) Int. Cl.
 *A61J 1/06* (2006.01)
 *A61M 5/31* (2006.01)
 *A61M 5/315* (2006.01)

(52) U.S. Cl.
 CPC ....... *A61M 5/31525* (2013.01); *G01F 23/261* (2013.01); *G01F 23/263* (2013.01); *G01F 23/268* (2013.01); *A61J 2200/76* (2013.01); *A61M 5/31593* (2013.01); *A61M 2005/3126* (2013.01); *A61M 2005/3142* (2013.01); *A61M 2205/3317* (2013.01); *A61M 2205/3389* (2013.01); *A61M 2205/3592* (2013.01); *A61M 2205/50* (2013.01); *A61M 2205/70* (2013.01); *A61M 2205/8206* (2013.01)

(58) Field of Classification Search
 CPC ...... A61M 2205/3592; A61M 2205/50; A61M 2205/70; A61M 2205/8206; A61J 1/065; A61J 2200/76; G01F 23/261
 USPC .......................................................... 73/304
 See application file for complete search history.

(56) References Cited

U.S. PATENT DOCUMENTS

| 9,395,716 | B2 | 7/2016 | Bammer et al. | |
| 2004/0189311 | A1* | 9/2004 | Glezer | B01L 3/5027 |
| | | | | 324/444 |
| 2008/0152507 | A1 | 6/2008 | Bohm | |
| 2009/0069756 | A1 | 3/2009 | Larsen | |
| 2010/0102799 | A1 | 4/2010 | Schnidrig | |
| 2014/0074062 | A1* | 3/2014 | Caffey | A61M 5/422 |
| | | | | 604/506 |
| 2014/0142537 | A1* | 5/2014 | Gibson | A61M 5/14546 |
| | | | | 604/500 |
| 2015/0045727 | A1 | 2/2015 | Bammer et al. | |

FOREIGN PATENT DOCUMENTS

| WO | 2007107558 A2 | 9/2007 |
| WO | 2013138830 A1 | 9/2013 |
| WO | 2014052997 A1 | 4/2014 |

* cited by examiner

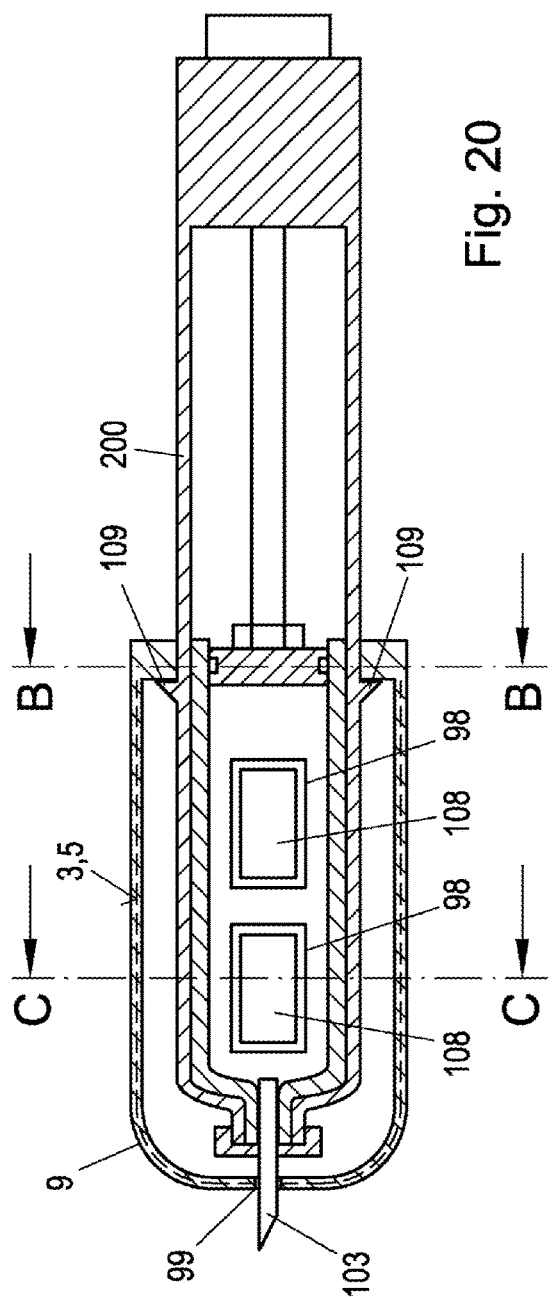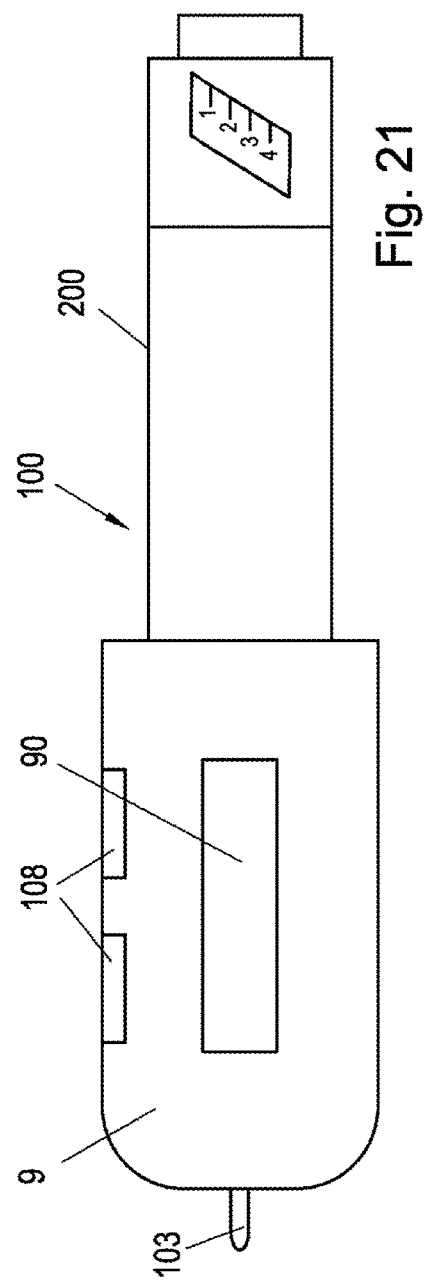

MEDICATION INJECTOR WITH CAPACITIVE FILL LEVEL MEASUREMENT CAPACITY, AND CONTACT SENSOR

BACKGROUND OF THE INVENTION

Field of the Invention

The invention relates to an administering apparatus for administering liquids, in particular liquid medicaments to persons. Furthermore, the invention relates to a cover cap for covering and shielding a container having a number of measuring electrodes and being filled with liquid. Finally, the invention relates to a method for determining and validating the filling level in a container which, in particular, is arranged in an administering apparatus.

The invention can be used, in particular, in the medical sector, for example in medical engineering, pharmaceutical technology and biotechnology, medicine and care, studies, etc., for monitoring the administration of medicaments to patients.

The prior art has disclosed various apparatuses for administering liquids, in which the amount of the administered liquid or the amount of liquid present in the administering apparatus is determined capacitively.

BRIEF SUMMARY OF THE INVENTION

It is an object of the present invention to effectively identify malfunctions in the case of capacitive filling level detection operations and facilitate an invalidation of capacitive filling level measurement results. Furthermore, it is an object of the invention to obtain results which are as good and reliable as possible.

In the case of an administering apparatus of the type set forth at the outset, the invention achieves this object by a container filled with the liquid, said container having an opening at one end for administering the liquid, and at least one pair of capacitive measuring electrodes arranged opposite one another in the outer region of the container, in particular abutting against the wall thereof, for determining the permittivity of the respective medium situated in the intermediate area between the measuring electrodes.

Moreover, in the case of a cover cap of the type set forth at the outset, the invention achieves the object by connection contacts, arranged on the cover cap, in particular on the inner side thereof, for electrically contacting the measuring electrodes, and at least one capacitance measuring device connected to the connection contacts.

Moreover, in the case of a method of the type set forth at the outset, the invention achieves the object by at least one pair of measuring electrodes, which are arranged opposite one another in the outer region of the container and, in particular, are provided with an outer shielding, are provided for measuring the capacitance, wherein the capacitance is established between the two measuring electrodes and a filling level value is determined in accordance with a predetermined calibration function on the basis of the established capacitance. A further capacitance is established by conductors arranged in the outer region of the measuring electrodes in the region of the shielding, in particular on the shielding, the further capacitance is compared to a threshold, and the filling level value is only considered to be valid if the further capacitance lies below the threshold.

According to the invention, the following are provided in an administering apparatus for administering liquids, in particular liquid medicaments to persons:

a container filled with the liquid, said container having an opening at one end for administering the liquid, and at least one pair of capacitive measuring electrodes arranged opposite one another in the outer region of the container, in particular at the wall thereof, for determining the permittivity of the respective medium in the intermediate area between the measuring electrodes. According to the invention, a stable and accurate establishment of the filling level of the liquid in the container is obtained.

Advantageously, provision can be made for the measuring electrodes to be surrounded by shielding arranged around the container. Malfunctions which are caused on account of capacitive effects by contacting the container during the measuring process are effectively avoided by way of the invention. In particular, by way of the measure according to the invention, it is possible to avoid that contacting of the measuring electrodes by the hands of a human or a falsification of the electric field in the region of the measuring electrodes by the hands of a human or other electrically conductive objects leads to changes in the filling level measurement value.

Advantageous protection of the measuring electrodes can be obtained by a cover cap surrounding the measuring electrodes and the container in a sheath-like manner.

In order to simultaneously obtain a mechanical and electrically effective protection of the measuring electrodes, provision can be made for the shielding to be integrated in the cover cap or applied to the surface of the cover cap.

Alternatively, provision can be made for the same purpose for the wall of the cover cap to surround the measuring electrodes and for the outer wall or outer surface of the cover cap to have a distance of at least 5 mm, in particular of at least 1 cm, from the measuring electrodes and/or to prevent access to, and contact with, the measuring electrodes.

Advantageously, the shielding can be embodied as a film coated with conductor tracks made of electrically conductive material. In a preferred embodiment, this film is arranged, or wound, around the container and/or surrounds the latter. Such shielding particularly advantageously prevents the falsification of measurement results.

In order to obtain good measurement results, provision can be made for the region between the liquid and the measuring electrodes to be free from the shielding.

In order to avoid a deterioration of the measurement results as a result of influences from the shielding, provision can be made for the shielding to be at a distance from the measuring electrodes in the radial direction.

In order to obtain improved shielding and, at the same time, facilitate fastening of a semiconductor chip and an antenna in the region of the shielding or on the film, provision can be made for the shielding to be embodied as a film coated with conductors in the form of conductor tracks, the film, in particular, being wound around the container, wherein, preferably, a capacitance measuring circuit, a computer unit and a communication controller, in particular in the form of a semiconductor chip, and an antenna are applied to the film.

In order to avoid a change in the electromagnetic field produced by an external data communication instrument, which impairs the radio communication with the antenna, and in order to simultaneously facilitate good electrical shielding of the measuring electrodes, provision can be made for the conductors to be embodied without loops and/or free from closed conductor loops.

For a good shielding effect, provision can be made for the conductors to have a width of at most 5 mm, in particular of between 0.1 mm and 3 mm, and a thickness of at most 3 mm, in particular of between 10 µm and 150 µm.

An electronically advantageous implementation of registering the filling level in the container provides for a communication controller and/or a number of capacitance measuring devices for establishing the capacitance between the measuring electrodes and/or a computer unit and/or an antenna for transferring measurement values established by the measuring electrodes or values derived therefrom, in particular filling level values, to be arranged on the film, and for these units arranged on the film to be preferably integrated in a common housing of a semiconductor chip.

A particularly advantageous configuration of shielding, which can be used for contact detection at the same time and moreover facilitates radio communication with an antenna applied to the shielding, provides for three separate conductors to be embodied on the film, wherein the first conductor and the second conductor are embodied as meshing comb conductors and the third conductor lies with a meandering form between the two comb conductors.

A preferred measure for determining the filling level of the liquid in the interior of the container provides for the two opposite measuring electrodes to be connected to a capacitance measuring device.

In order to easily establish the filling level, provision can be made for the capacitance value established by the capacitance measuring device to be fed to a computer unit which, on account of the established capacitance value, determines the filling level of the liquid in the container by means of a predetermined stored calibration function and keeps said filling level available at the output thereof.

Particularly effective shielding with a good shielding effect may be obtained by virtue of one of the three conductors, in particular the second conductor embodied as a comb conductor, being connected to the ground connector of the capacitance measuring device.

In order to be able to advantageously determine contacts or falsifications of the capacitance measurement, provision can be made of a contact sensor, in particular a capacitive contact sensor, arranged outside, or in the region of, the shielding.

A variant that is easy to manufacture from a production-technological point of view provides for the contact sensor to comprise the first comb conductor and the meandering conductor of the shielding as sensor electrodes.

Here, for the detection of contacts, provision can be made for the sensor electrodes of the contact sensor to be connected to a further capacitance measuring device and for, preferably, the further capacitance value established by the further capacitance measuring device to be fed to the computer unit and for the computer unit to suppress, or characterize as invalid, the forwarding of the filling level established thereby in the case where the established further capacitance value exceeds a predetermined threshold.

An advantageous container for receiving liquids, which can be easily emptied and the filling level of which can easily be determined, provides for the container to have an interior volume which, apart from the region of the opening, has a constant internal cross section, wherein provision is made of a plunger which terminates and seals the container and the liquid situated therein, the external cross section of said plunger corresponding to the cross section of the interior volume of the container and said plunger being displaceably arranged in the interior of the container such that the liquid is administered from the container through the opening when the plunger is advanced towards the opening.

In order to determine the filling level more precisely, provision can be made for a multiplicity of pairs of additional measuring electrodes to be arranged at the container, wherein, in particular, provision is made in each case of an additional capacitance measuring device disposed downstream of the pair of additional measuring electrodes for each pair of additional measuring electrodes, said capacitance measuring device outputting the established capacitance value to the computer unit.

An advantageous electrode arrangement, which facilitates an accurate filling level determination, provides for the measuring electrodes, assigned to one another in pairs in each case, to lie opposite one another, in particular diametrically opposite one another, in the circumferential direction of the container and, in particular, to lie at the same position or level in the direction of advance of the plunger.

For the purposes of increasing the detection accuracy, provision can additionally be made here for respectively adjacent pairs of measuring electrodes to be arranged at a distance from one another in the direction of advance of the plunger and/or for the width of the measuring electrodes in the direction of advance of the plunger to correspond to the width of the plunger in the advance direction thereof.

Preferred embodiments of the measuring electrodes with a simple setup provide for the measuring electrodes to be arranged extensively on the outer surface of the container and, in particular, to have the form of a quadrilateral, a triangle, a trapeze or a parallelogram, and/or for two of the measuring electrodes assigned to one another in pairs to be respectively formed by two meshing comb conductors which are arranged in the outer region of the container, in particular at the outer wall thereof.

In order to facilitate a simple interchange of the containers, provision can be made for a carrier on which the measuring electrodes are arranged to be arranged outside of the container between the container and the shielding, wherein the carrier preferably abuts against the container and/or for the measuring electrodes to be arranged on the wall of the carrier abutting against the container, wherein, in particular, part of the housing of the administering apparatus is embodied as a carrier or the carrier is connected to the housing.

Advantageously, the established filling level may be transferred to an external communication instrument. Here, provision can be made for a communication controller with an antenna disposed downstream thereof to be connected to the computer unit. Advantageously, for a more space-saving arrangement, provision can be made for the antenna to be arranged in the outer region of the shielding or directly on the shielding, but not to be electrically conductively connected to the latter.

An administering apparatus with a simple setup, which has a reusable cover cap for measuring the filling level and, optionally, displaying the latter, provides for the cover cap to have a number of electrical contacts which are each electrically conductively connected to one of the measuring electrodes of the container, in particular by way of connection contacts arranged on the cover cap.

A simple solution in terms of production technology provides for the shielding and/or the conductors, the capacitance measuring devices and/or the further capacitance measuring device and/or the computer unit and/or the communication controller and/or the antenna and/or a voltage supply to be integrated into the cover cap.

In order to facilitate a good hold between cover cap and the body of the administering apparatus, provision can be made for the cover cap to have a continuous recess for administering liquid through the cover cap in the region of the opening of the container, with, where required, an injection needle which is in contact with the liquid being guided through said recess, and/or for the cover cap to surround the container and, in particular, an injection needle which is in contact with the liquid, and/or for the cover cap to be connectable to the container and/or to a housing part adjoining the container, in particular in a manner which is detachable a number of times, and/or for the cover cap to be embodied in the form of a sleeve which is open at the end of the injection needle.

In order to be able to observe the container during the administering and/or measuring process and in order to be able to identify possible turbidity of the liquid situated in the container or foreign bodies, provision can be made for a viewing window, through which the liquid is visible, to be provided in the carrier body, wherein, where necessary, the cover cap has a further viewing window, through which the liquid is visible, in the region of the viewing window, and/or for a display unit to be provided in the outer region of the cover cap, said display unit, in particular, indicating the filling level of the liquid in the interior of the container.

Furthermore, the invention relates to a cover cap for covering and shielding a container having a number of measuring electrodes and filled with liquid, said cover cap comprising connection contacts, arranged on the cover cap, in particular on the inner side thereof, for electrically contacting the measuring electrodes, at least one capacitance measuring device connected to the connection contacts.

Using such a reusable cover cap, it is possible to undertake a multiple measurement of different containers in different carrier bodies. Particularly in the case of sets with a plurality of containers, it is possible to prevent a multiple realization of a measuring device on all carrier bodies.

A particularly advantageous arrangement provides shielding extending in the interior of the cover cap or on the surface thereof, said shielding, in particular, being connected to a further capacitance measuring device.

An advantageous cover cap, with which automatic further-processing of data is possible directly on the cover cap, provides the following:

a computer unit disposed downstream of the capacitance measuring device or the capacitance measuring devices and/or the further capacitance measuring device, and where necessary, a communication controller disposed downstream of the computer unit, with, in particular, an antenna being connected thereto.

Advantageously, a voltage supply arranged on or in the cover cap may be provided, said voltage supply being connected to the capacitance measuring device and, optionally, to the further capacitance measuring device and/or the computer unit and/or the communication controller, and supplying these with electrical energy.

In order to advantageously facilitate administering liquid out of the container, provision can be made for a recess which is continuous through the cover cap and situated, in particular, in the region of the opening of the container to be provided for administering liquid through the cover cap and/or for the cover cap to be embodied in the form of a sleeve, which is open on one side.

In order to ensure multiple use of the cover cap, provision can be made for the cover cap to be embodied for detachable connection, in particular connection which is detachable a number of times, to the container or to a housing part connected thereto.

In order to be able to observe the container during the administering and/or measuring process and in order to be able to identify possible turbidity of the liquid situated in the container or foreign bodies, provision can be made for a viewing window, through which the liquid situated in the interior of the cover cap and the container is visible from the outside, to be provided.

Alternatively, or additionally, provision can also be made for a display unit to be provided in the outer region of the cover cap, which, in particular, indicates the filling level of the liquid in the interior of the container.

Furthermore, the invention relates to a method for determining and validating the filling level in a container which, in particular, is arranged in an administering apparatus according to the invention, wherein at least one pair of measuring electrodes, which are arranged opposite one another in the outer region of the container and, in particular, are provided with an outer shielding, are provided for measuring the capacitance, wherein the capacitance is established between the two measuring electrodes and a filling level value is determined in accordance with a predetermined calibration function on the basis of the established capacitance.

According to the invention, provision is made in such a method for a further capacitance to be established by means of conductors arranged in the outer region of the measuring electrodes in the region of the shielding, in particular on the shielding, for the further capacitance to be compared to a threshold, and for the filling level value to be only considered to be valid if the further capacitance lies below the threshold.

Using such a method, it is easy to check whether the established filling level value was falsified by virtue of a person touching the measuring electrodes or the shielding in the region of the measuring electrodes or coming sufficiently close to the measuring electrodes to cause falsification.

In order to exactly determine the filling level, provision can be made for the filling level value and/or a statement about the validity of the filling level value to be transferred by encoded electromagnetic data transfer, in particular by load modulation, to an external data communication instrument.

For the same purpose, provision can be made for the capacitances from a multiplicity of pairs, in particular three pairs, of measuring electrodes to be established in each case and for the filling level value to be established on the basis of the capacitances, wherein the measuring electrodes assigned to one another in pairs lie opposite one another in the outer region of the container.

A particularly exact detection is facilitated by virtue of a) reference vectors comprising the capacitances between the individual pairs of measuring electrodes as components being provided in each case for a number of filling levels and b) the respective filling level being assigned to each one of these vectors, c) a vector comprising the individual established capacitances being established, d) a number of reference vectors being sought after, said reference vectors having the smallest distance, in particular Euclidean distance, from the vector, e) an interpolation function being formed which, when applied to the reference vectors found in step b), yields the respective filling level assigned to these reference vectors, f) the interpolation function being applied to the vector and the result being used as filling level.

BRIEF DESCRIPTION OF THE SEVERAL VIEWS OF THE DRAWING

A plurality of preferred embodiments of the invention are explained in more detail on the basis of the following figures in the drawing.

FIG. 20 shows a further embodiment of the invention with a cover cap. FIG. 21 shows an external view of the embodiment depicted in FIG. 20.

DESCRIPTION OF THE INVENTION

Figure 1:
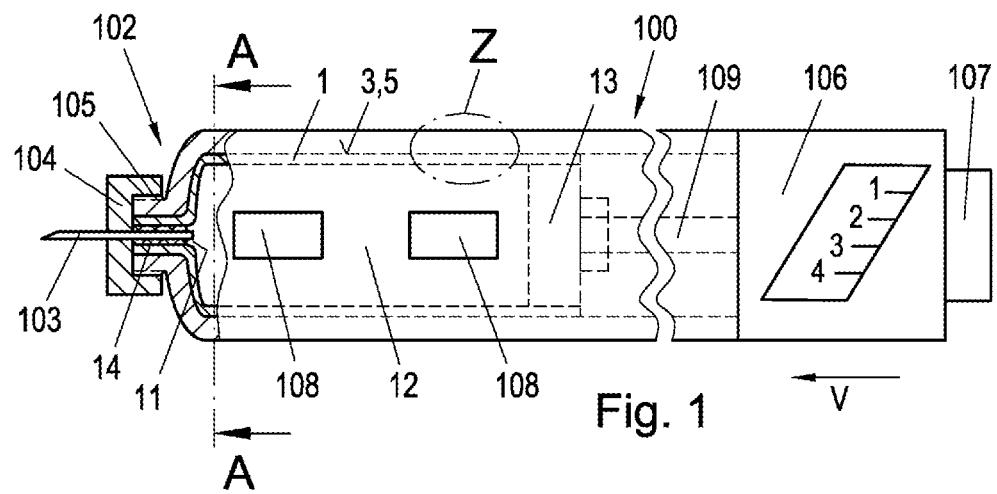
FIG. 1 depicts a side view of a first embodiment of an administering apparatus according to the invention.

FIG. 1 depicts a side view of an embodiment of an administering apparatus 100 according to the invention. The depicted administering apparatus 100 has a container 1, which is filled with a liquid medicament 12. In the present case, insulin is used as liquid medicament 12; however, it is also possible to fill other liquid medicaments 12, such as hormone preparations (e.g. growth hormones, etc.), biopharmaceuticals or medicaments used within the scope of therapeutic measures in reproductive medicine, into the container 1 and subsequently administer these in the same way.

The administering apparatus 100 has the form of a pencil or pen and can be comfortably held in the hand by a patient when administering the liquid 12 situated in the container 1. The container 1 has the form of a cartridge or ampoule and is situated in an end region 102 of the administering apparatus 100.

Figure 2:
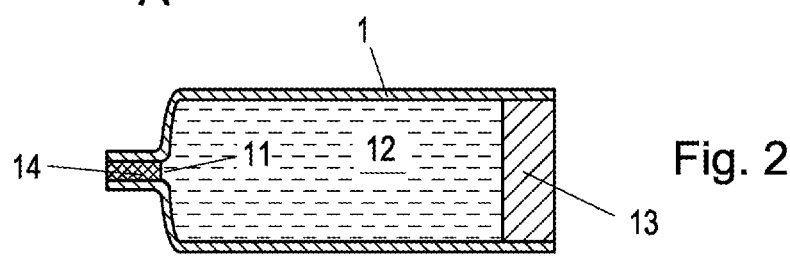
FIG. 2 shows a side view of a completely filled container in the form of an ampoule.

The container 1, which is depicted in detail in FIG. 2, has an opening 11 for administering the liquid 12 at one end which lies in this end region 102 of the administering apparatus 100. At the opposite end, the container 1 has a plunger 13 which is mounted in the container 1 in a displaceable manner. To this end, the container 1 has an internal volume which, apart from the region of the opening 11, has a constant cross section. The plunger 13 seals the container 1 from the side opposite to the opening 11 in such a way that the liquid 12 situated in the container 1 is securely enclosed in the container 1 and can only escape through the opening 11. In the present exemplary embodiment, the inner regions of the container 1 and of the plunger 13 have a circular cross section and comprise a substantially cylindrical inner wall or outer wall. If the plunger 13 is inserted or advanced into the container 1, the liquid 12 situated in the container 1 can escape from the container 1 through the opening 11. The liquid 12 is administered from the container 1 through the opening 11 when the plunger 13 is advanced in the direction of the opening 11. However, as depicted in FIG. 2, the opening 11 of the container 1 is sealed by a sealing element 14 prior to use such that the liquid 12 cannot escape from the container 1.

Figure 3:
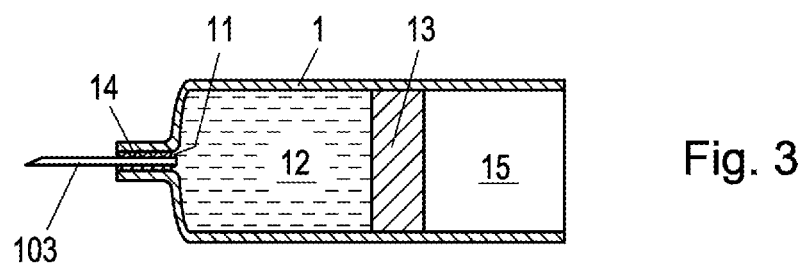
FIG. 3 shows a side view of a partially emptied container.

FIG. 3 shows the container 1 depicted in FIG. 2 after some of the liquid 12 was applied through the opening 11 by way of an injection needle 103.

Figure 4:
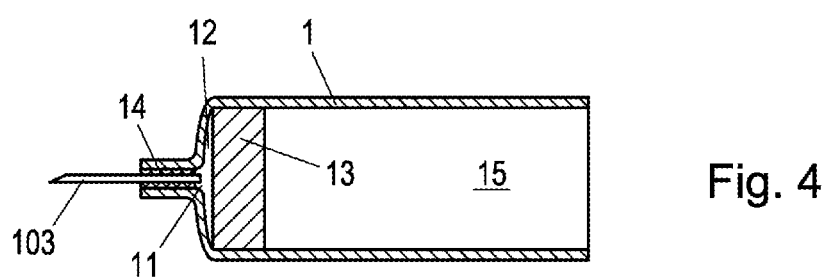
FIG. 4 shows a side view of a completely emptied container.

FIG. 4 shows the container 1 depicted in FIG. 2 after the liquid 12 was completely emptied from the container 1 through the opening 11 by way of an injection needle 103. In the illustrations of FIG. 3 and FIG. 4, the plunger 13 is situated in a mid position or in an end position, i.e. the container 1 is emptied in part (FIG. 3) or completely (FIG. 4). Air is situated in the region 15 behind the plunger 13. The administering apparatus 100 furthermore has an injection needle 103 in the region of the opening 11 of the container 1, said injection needle, firstly, penetrating the sealing element 14 and projecting into the interior of the container 1 and, secondly, protruding from the administering apparatus 1.

As depicted in FIG. 1, the injection needle 103 in this exemplary embodiment is connected to a housing 104 which is screwed onto the administering apparatus 100. The administering apparatus 100 has a male thread 105, which is fitted to a fitting female thread of the housing 104 with an opposite form. If the plunger 13 is displaced in the direction of the opening 11, as depicted in FIG. 3, the liquid situated in the interior of the container 1 may be administered to the respective patient through the opening 11 and the injection needle 103. The housing of the administering apparatus 100 has two viewing openings 108 in order to be able to visually determine the filling level F of the residual liquid 12 situated in the container 1 or to be able to identify possible turbidity or foreign bodies in the liquid 12.

Moreover, the administering apparatus 100 (FIG. 1) has an adjustment unit 106, by means of which it is possible to set in advance a specific advance of the plunger 13 and—corresponding therewith—a certain amount of the liquid 12 to be administered. After setting the amount of liquid 12 to be administered, an advance element 109 is pressed against the plunger 13 of the container 1 by way of the patient actuating pressure onto an actuation unit 107. The plunger 13 is pushed into the container 1 and the liquid 12 situated in the container 1 is administered to the patient by way of the injection needle 103. The advance element 109 is secured against a reset against the direction of advance V of the plunger 13, i.e. away from the opening 11, and so the plunger 13 can only be moved further in the direction of the opening 11.

Figure 5:
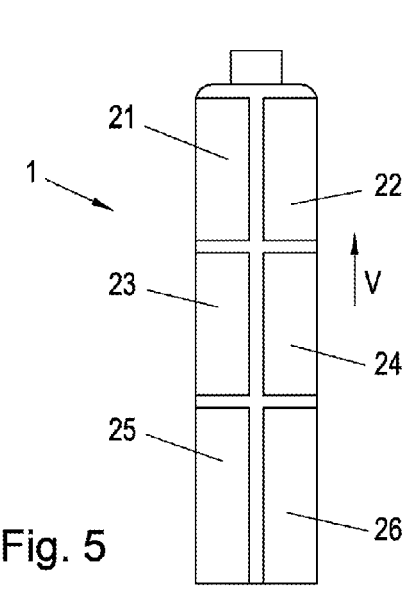
FIG. 5 shows an alternative embodiment of a container with three pairs of measuring electrodes.

The use of a container 1 with three pairs of measuring electrodes, as depicted in FIG. 5, may be particularly advantageous. As depicted in FIG. 5, the container 1 has three pairs of measuring electrodes 21-26. All measuring electrodes 21-26 are arranged in the outer region of the container 1, on the outer wall of the container 1 in the present case. In this preferred exemplary embodiment of the invention, two measuring electrodes 21-26 assigned to one another in each case lie opposite one another, spaced apart in the circumferential direction, on the outer wall of the container 1. The individual pairs of measuring electrodes 21-26 assigned to one another are spaced apart from one another in the direction of advance V of the plunger 13. The measuring electrodes 25, 26 of the third pair lie furthest away from the opening 11 of the container 1. The measuring electrodes 21, 22 of the first pair lie closest to the opening 11. As seen in the direction of advance V of the plunger 13, the measuring electrodes 23, 24 of the second electrode pair lie between the measuring electrodes 21, 22; 25, 26 of the first pair and of the third pair. The measuring electrodes 21-26 lie extensively on the outer wall of the container 1 in a region thereof. In the exemplary embodiment depicted in FIG. 5, the measuring electrodes 21-26 have a rectangular form. The measuring electrodes 21-26 extend over the whole range of advance of the plunger 13. If a plurality of pairs of electrodes are used, it may be advantageous if the extent of one of the electrode pairs in the direction of advance V of the plunger 13 corresponds to the extent of the plunger 13 in the direction of advance V thereof.

Figure 6:
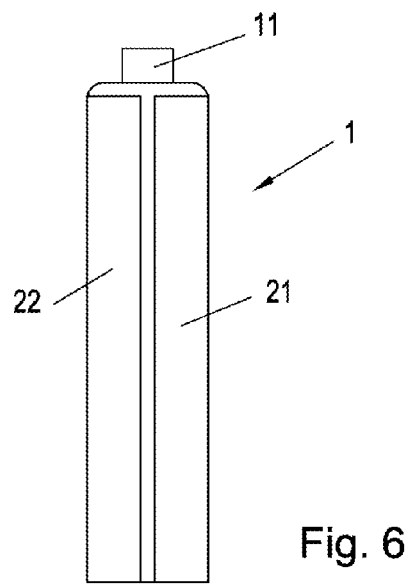
FIG. 6 shows a second embodiment of the invention with a single pair of measuring electrodes.

However, alternatively, it is also possible to use other electrode forms, e.g. circular or comb-like electrode forms, for the measuring electrodes 21-26. Although, as a matter of principle, the use of a plurality of pairs of measuring electrodes 21-26 within the scope of an accurate measurement of the liquid content or liquid level is advantageous in the case of elongate containers 1, it is not mandatory, especially in the case of short or compact containers 1. In an alternative exemplary embodiment of a container 1, depicted in FIG. 6, provision is made of merely a single pair of measuring electrodes 21, 22, which have an embodiment that is elongate and extends over the entire range of advance. The two measuring electrodes 21, 22 lie opposite one another on the circumferential side, at the same level or position in view of the direction of advance V of the plunger 13.

Figure 7:
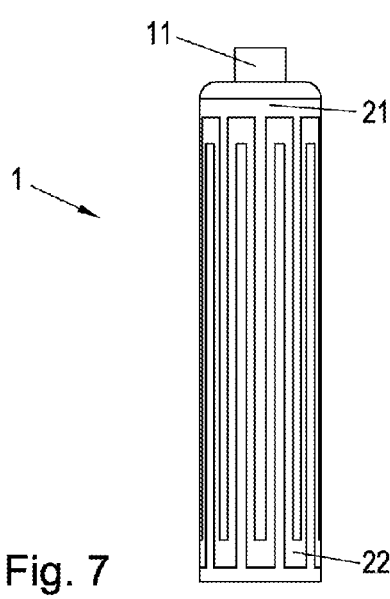
FIG. 7 shows a further embodiment of the invention with one pair of measuring electrodes arranged in a comb-shaped manner.
Figure 8:
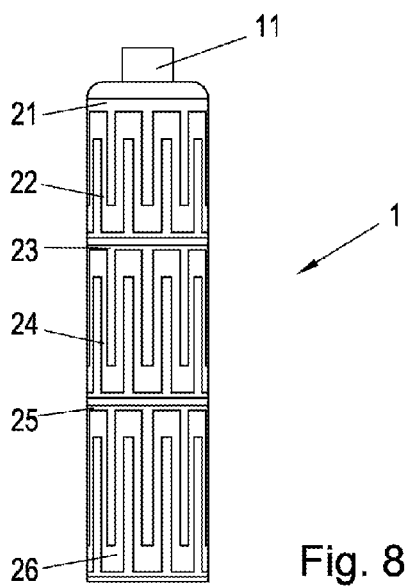
FIG. 8 shows a further embodiment of the invention with three pairs of measuring electrodes arranged in a comb-shaped manner.
Figure 9A:
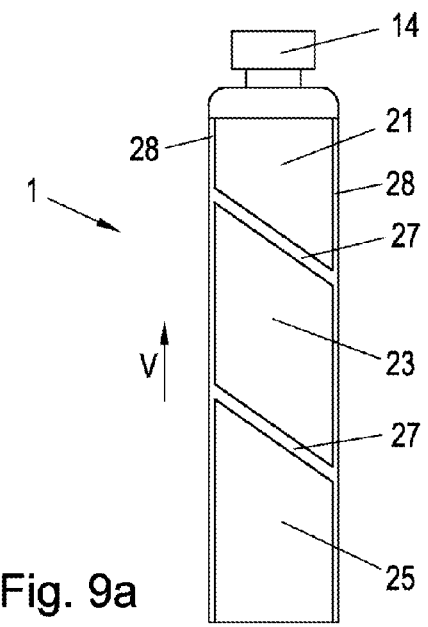
FIGS. 9a to 12d show further embodiments of containers with obliquely extending electrodes.
Figure 9B:
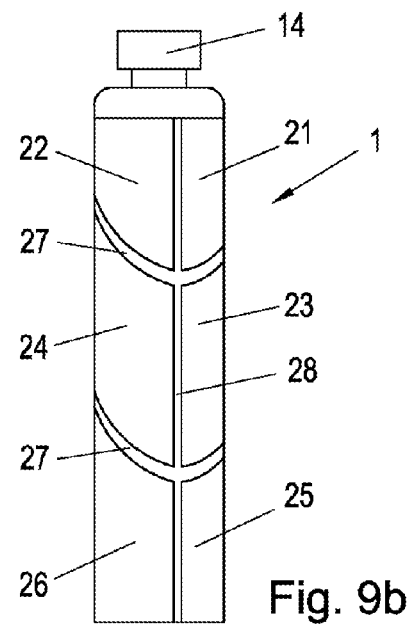
Figure 9C:
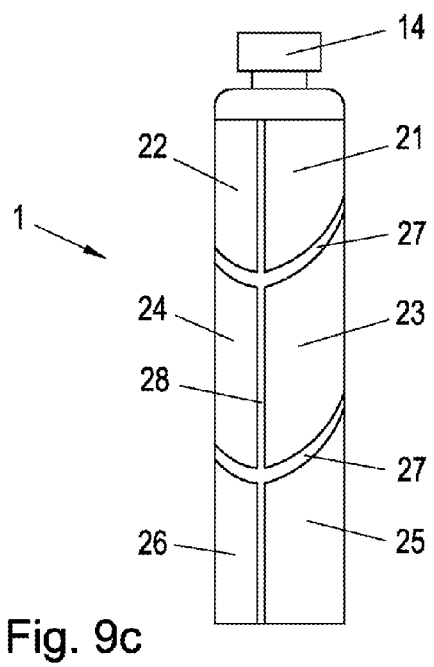
Figure 9D:
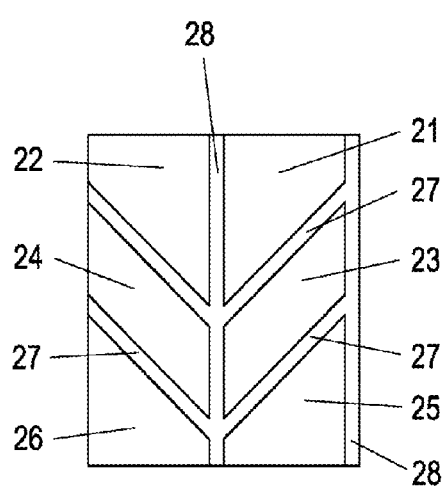
Figure 10A:
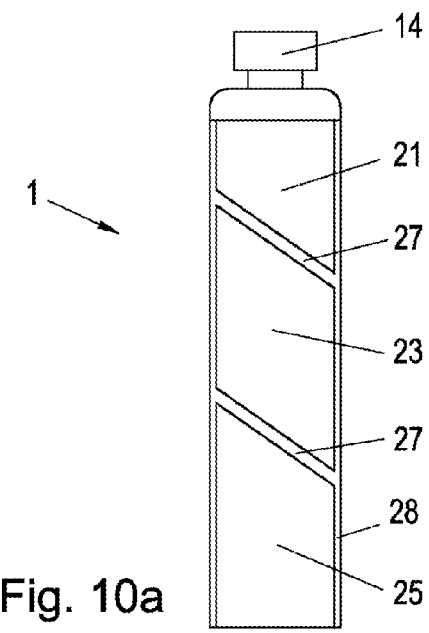
Figure 10B:
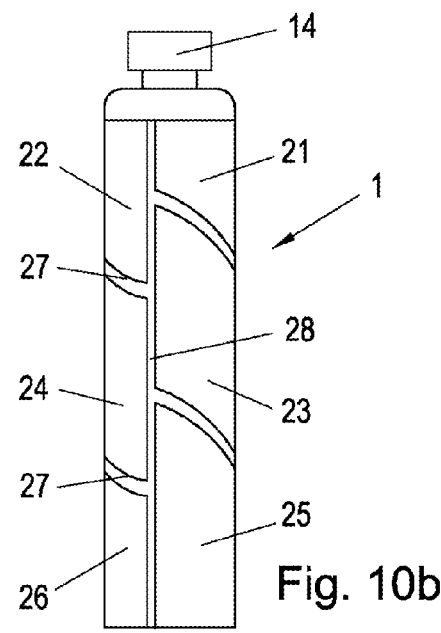
Figure 10C:
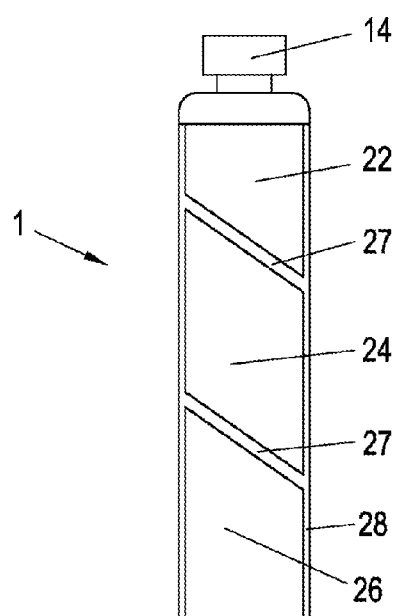
Figure 10D:
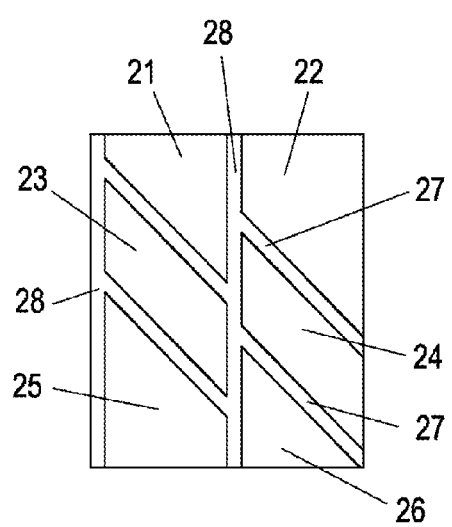
Figure 11A:
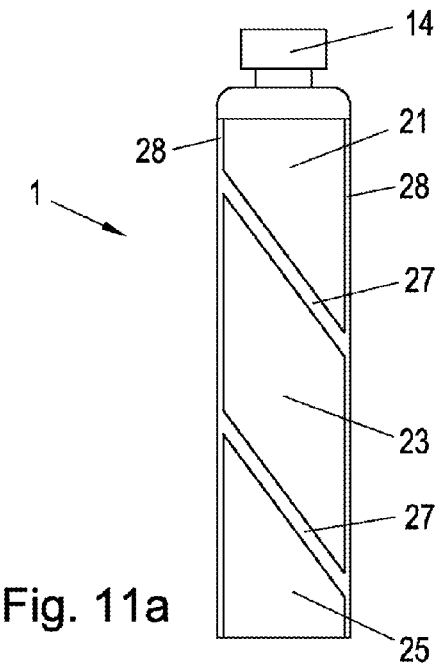
Figure 11B:
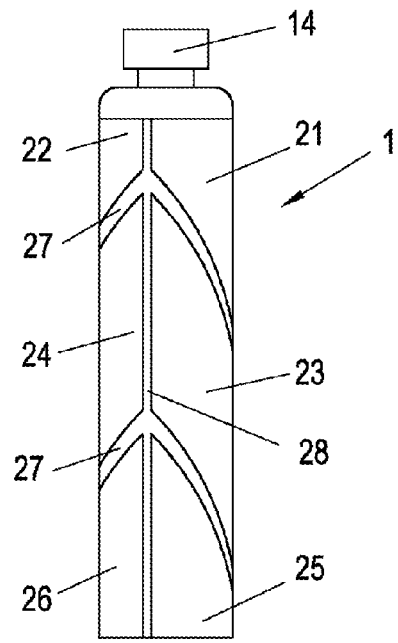
Figure 11C:
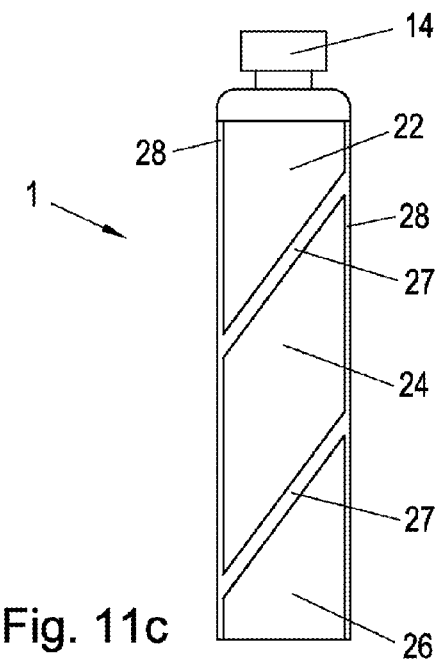
Figure 11D:
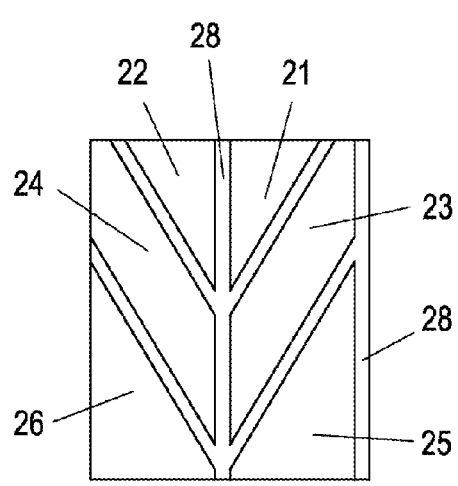
Figure 12A:
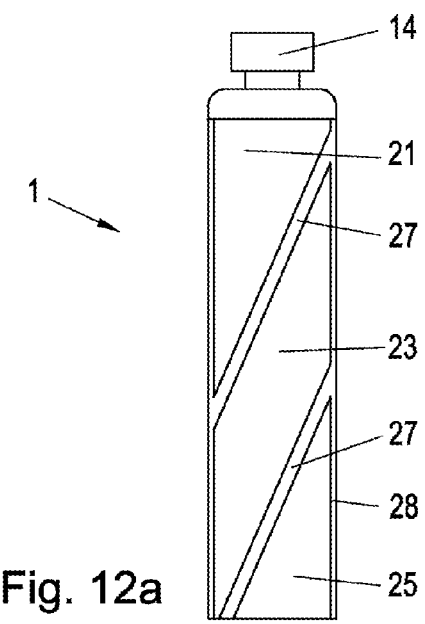
Figure 12B:
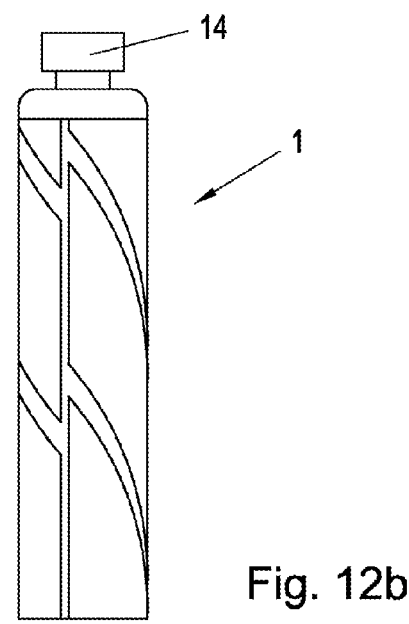
Figure 12C:
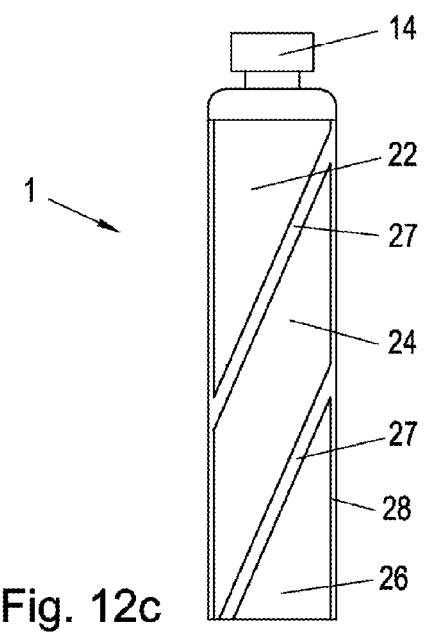
Figure 12D:
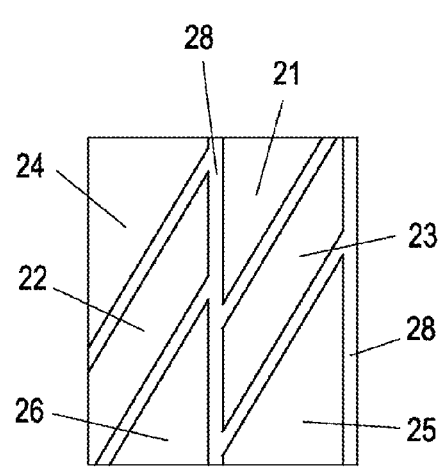

Moreover, it is also possible to use different forms of measuring electrodes 21-26. One advantageous embodiment provides for the measuring electrodes 21-26 to be embodied as comb electrodes or interdigital electrodes. The measuring electrodes 21-26 are assigned to one another in pairs and have a comb structure, with the teeth of measuring electrodes 21, 22; 23, 24; 25, 26 assigned to one another meshing. As depicted in FIG. 7 and FIG. 8, comb electrodes can be used both for an arrangement with one pair (FIG. 7) and with several pairs of measuring electrodes 21, 22; 23, 24; 25, 26.

Depending on the case of application, it is also possible to provide measuring electrodes 21-26 with different dimensions in order to facilitate a particularly advantageous determination of the filling level F in the container 1. The use of parallelogram-shaped or triangular measuring electrodes 21-26, in which the electrodes are separated from one another by separation regions 27 which extend at an angle in relation to the direction of advance V of the plunger or the longitudinal axis of the container 1, for example at an angle of 45°, is particularly advantageous. In the case of such an arrangement, there is a smooth transition, and so a particularly accurate determination of the filling level F becomes possible. FIGS. 9a to 12d show four different embodiments with separation regions 27, which are at an angle to the direction of advance V, between the measuring electrodes 21-26. Furthermore, these embodiments provide for a separation region 28 parallel to the axis, which separates from one another pairs of measuring electrodes 21, 22; 23, 24; 25, 26 assigned to one another in each case.

Figure 13:
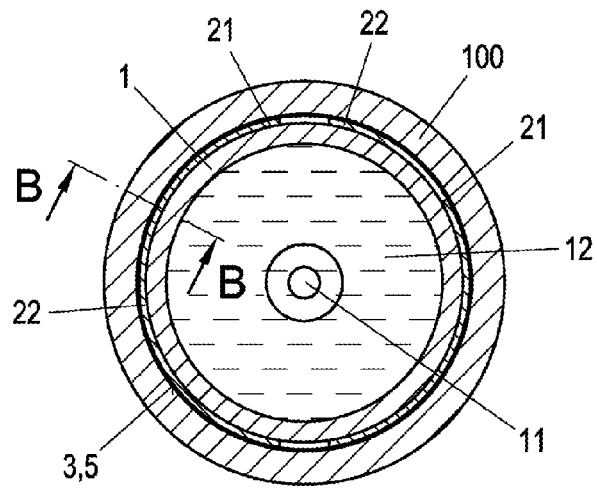
FIG. 13 shows an exemplary embodiment of an apparatus according to the invention in the cross section B-B.

With all of these electrode arrangements it is possible to deduce the filling level F of the container 1 due to the capacitance between the measuring electrodes 21-26. In order to facilitate a measurement of the individual capacitances $C_1$, $C_2$, $C_3$ which is as precise as possible and therefore be able to draw conclusions about the filling level F of the container 1, the invention, in the case of an administering apparatus, provides for electrical shielding 3 for electric fields outside of the measuring electrodes 21-26 to be arranged around the container 1 in a sheath-like manner. FIG. 13 depicts a section through the container 1, which depicts the shielding 3, the measuring electrodes 21, 22, the wall of the container and the liquid 12 in the interior of the container 1. The shielding 3 causes the capacitance measured between the electrodes 21, 22 not to be falsified, or only to be falsified to a negligible extent, if a person touches the administering apparatus 100 or comes close thereto and, as a result thereof, modifies the electric field conditions prevailing at the measuring electrodes 21, 22. In a first exemplary embodiment of the invention, the shielding 3 is embodied as a film made of electrically conductive material, for example as a copper film with a thickness of 50 μm, which is wound around the container 1, and the measuring electrodes 21, 22 abutting thereon, in a sheath-like manner. The measuring electrodes 21, 22 and the shielding 3 are separated from one another and not connected to one another in an electrically conductive manner. The shielding 3 serves to suppress the influence of external influences, e.g. changes in the permittivity and electric fields in the immediate outer region of the measuring electrodes 21, 22. The shielding 3 surrounds both the measuring electrodes 21, 22 and the container 1 and is advantageously not situated between the measuring electrodes and the container 1. In particular, radial spacing between the shielding 3 and the measuring electrodes was found to be advantageous. Furthermore, it is not necessary to embody the shielding 3 as an all-over electrically conductive film; instead, it is also possible to realize the shielding 3 in the form of individual conductor tracks arranged on a non-electrically-conductive carrier material, such as e.g. a non-electrically-conductive film.

Figure 13A:
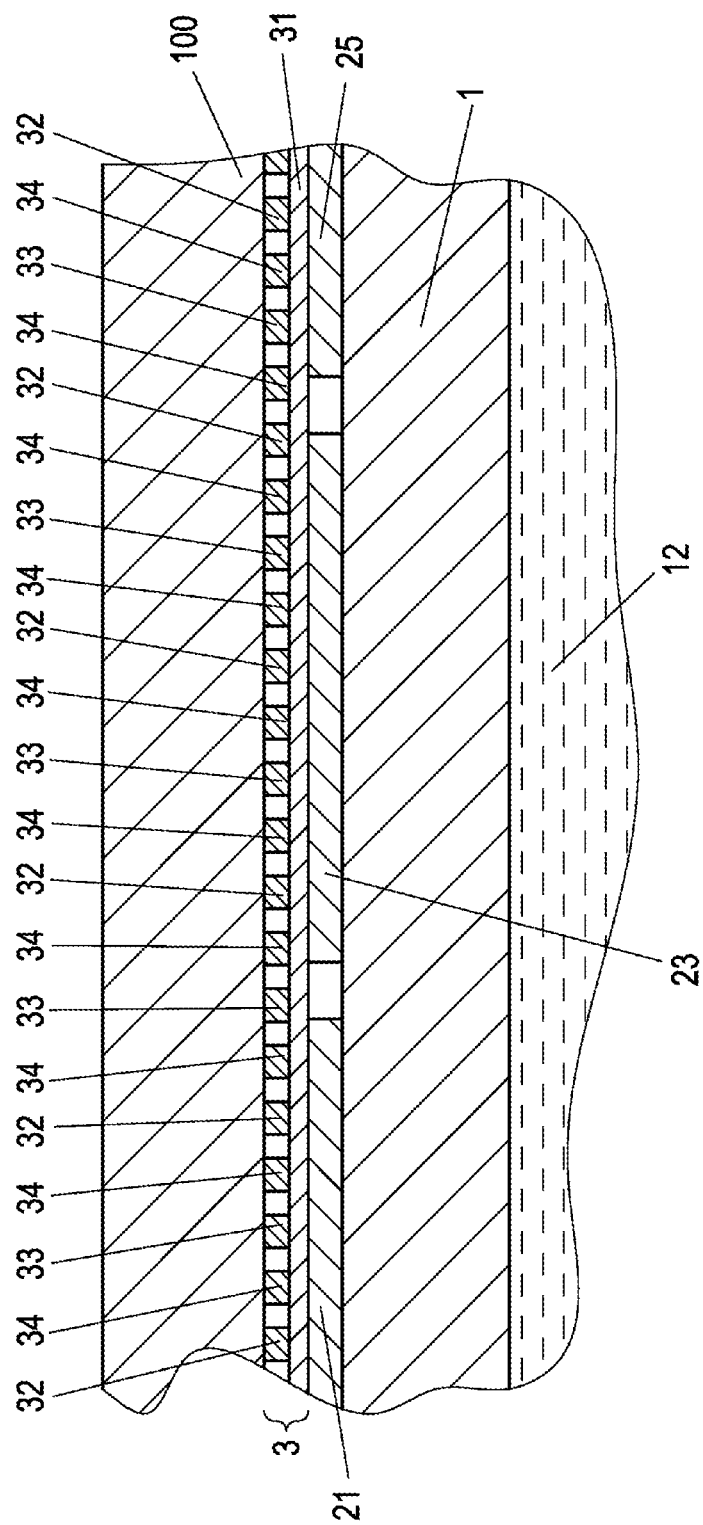
FIG. 13a shows a detail Z from FIG. 1.

FIG. 13a shows the detail Z from FIG. 1 in the section B-B of FIG. 13. It is possible to clearly identify—albeit not with the correct scale—the arrangement of the wall of the container 1 in relation to the electrodes 21, 23, 25 and the shielding 3. The individual conductors 32-34 on the film 3 are depicted in section. The housing of the administering apparatus 100 is situated outside of the shielding 3.

Alternatively, it is also possible to arrange the shielding 3 directly outside of the outer wall of the administering apparatus 100 and/or outside of a carrier 31 at least partly surrounding the container 1. The carrier 31 in this case serves to provide a radial spacing between the shielding 3 and the measuring electrodes 21, 22 at the same time.

Figure 14:
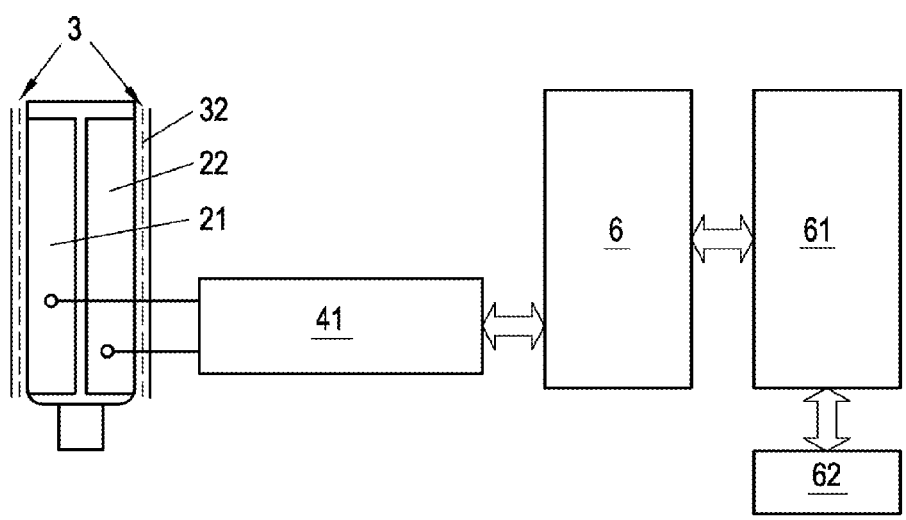
FIG. 14 and FIG. 15 show two devices for determining the filling level within the container and for transferring the established filling level to an external data communication instrument.
Figure 15:
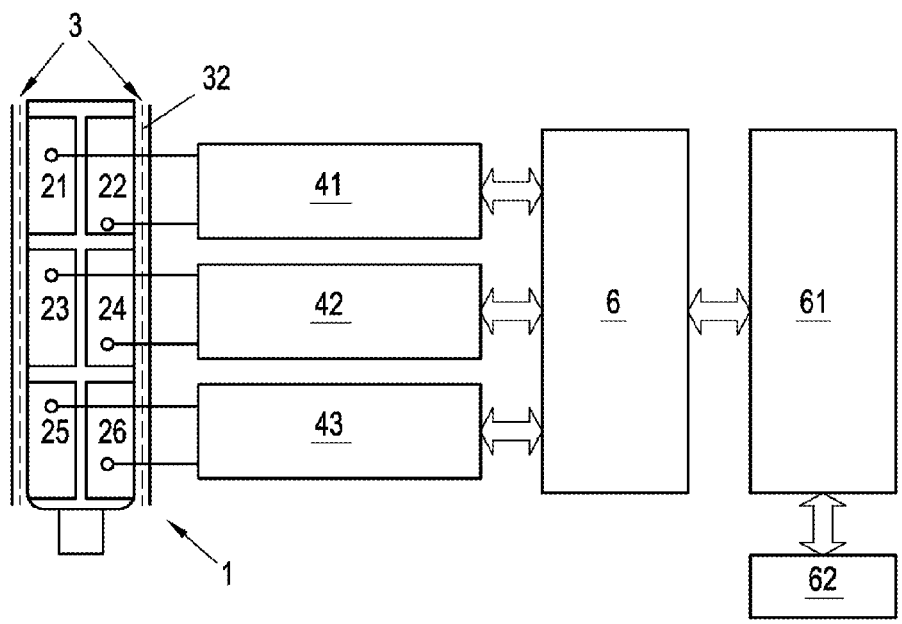

For the purposes of determining the current filling level F of the liquid 12 in the container 1, the present capacitance between the measuring electrodes 21, 22 is determined first. FIG. 14 depicts a measuring arrangement for determining the capacitance of a single pair of measuring electrodes 21, 22. FIG. 15 shows a measuring arrangement when using a plurality of pairs of measuring electrodes 21-26. Provision is respectively made in FIGS. 14 and 15 of a computer unit 6 in the form of a microcontroller, with one or three capacitance measuring devices 41, 42, 43 being disposed upstream thereof. One of the capacitance measuring devices 41, 42, 43 depicted in FIG. 15 is in each case assigned to each pair of measuring electrodes 21-26. The measuring electrodes 21-26 are each connected to the connectors of the capacitance measuring devices 41, 42, 43. A capacitance measurement value $C_1$, $C_2$, $C_3$ corresponding to the respective capacitance of the respective electrode pair, representing the latter or being proportional thereto, is in each case available at the output of the capacitance measuring devices 41, 42, 43, said capacitance measurement value being transferred to the computer unit 6. On the basis of a calibration process described below, the computer unit 6 establishes a value for the filling level F on account of the individual transferred capacitance measurement values $C_1$, $C_2$, $C_3$. The computer unit 6 keeps this value available at the output thereof. In particular, upon request, this value can be transferred to an external data communication instrument (not depicted here) by way of an antenna 62 disposed downstream of the computer unit 6.

Naturally, the number of pairs of measuring electrodes 21-26 used can be adapted to the requirements on the accuracy of the measurement. In particular, it is also possible to use a single pair of measuring electrodes 21, 22 and only to use the capacitance measurement value $C_1$ established between these measuring electrodes 21, 22 for the purposes of determining the filling level F (FIG. 15).

A communication controller 61, which is connected to an antenna 62, is disposed downstream of the computer unit 6. The communication controller 61 facilitates the transfer of the established filling level F to an external data communication instrument. As an alternative to the wireless transfer of data relevant to the filling level to an external data communication instrument, a wired transfer according to the prior art, such as e.g. USB, is naturally also possible. Moreover, provision can also still be made for the external data communication instrument to transfer electrical energy to the communication controller 61, the computer unit 6, and the capacitance measuring devices 41-43 by way of the antenna 62, such that the entire circuit depicted in FIG. 14 or FIG. 15 makes do without a separate energy supply.

Figure 17:
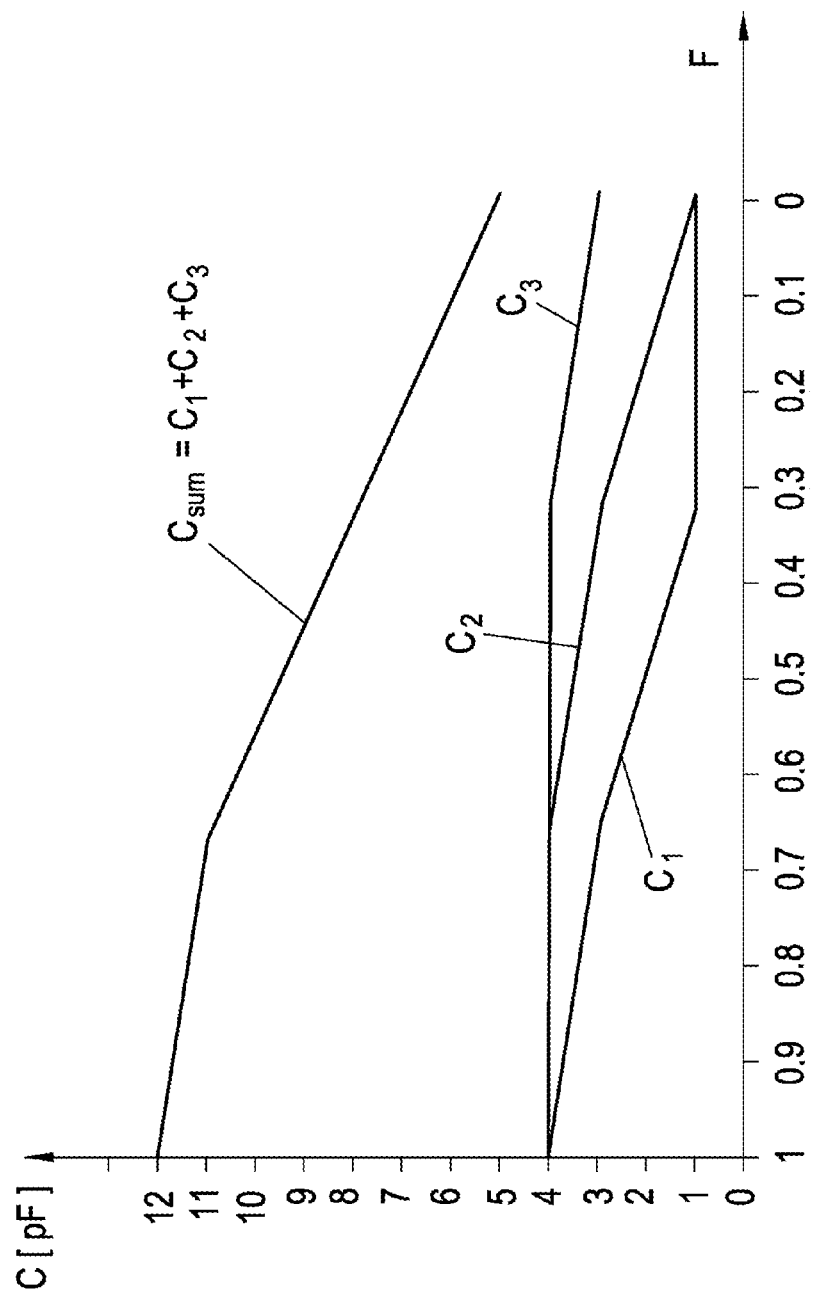
FIG. 17 shows the theoretical curve of the individual partial capacitances when emptying the container in the embodiment depicted in FIG. 15.

Below, how the filling level F of the liquid 12 in the container 1 is specifically established is depicted in more detail on the basis of the established capacitance measurement values $C_1$, $C_2$, $C_3$. FIG. 17 in each case schematically depicts the dependence of the individual capacitance measurement values $C_1$, $C_2$, $C_3$ on the filling level F in the embodiment of a container 1 according to the invention as depicted in FIG. 5. At the start of the emptying process of the container 1, the liquid 12 is initially exclusively situated between the measuring electrodes 21-26. Within the scope of emptying, the plunger 13 initially reaches the intermediate area between the measuring electrodes 21, 22 of the first measuring electrode pair, and so it is possible to observe a continuous drop in the capacitance measurement value $C_1$ of the first measuring electrode pair on account of the lower permittivity of the plunger 13 in relation to the liquid 12. After the plunger 13 was pushed through the intermediate area between the measuring electrodes 21, 22 of the first measuring electrode pair, air 15 is situated between the two measuring electrodes 21, 22 of the first measuring electrode pair. On account of the even lower permittivity of the air between the two measuring electrodes 21, 22 of the first measuring electrode pair, the capacitance measurement value $C_1$ measured between these measuring electrodes 21, 22 drops even further. A similar behavior can also be noted for the capacitance measurement values $C_2$, $C_3$ between the measuring electrodes 23-26 of the second and third measuring electrode pair when emptying the container 1.

In a particular embodiment of the invention, the sum $C_{sum}$ of the individual capacitance measurement values $C_1$, $C_2$, $C_3$ can be used to determine the filling level F. By establishing a calibration curve, it is possible to establish, in each case, the associated sum $C_{sum}$ of the individual capacitance measurement values $C_1$, $C_2$, $C_3$ for a number of different filling levels, with a sum $C_{sum}$ being assigned to each filling level F in each case. The individual data records produced thus, each comprising a capacitance measurement value $C_{sum}$ and a filling level F, are stored in a calibration memory in the computer unit 6.

Alternatively, it is also possible to keep the individual calibration data records, each comprising a capacitance measurement value $C_{sum}$ and a filling level F, available outside of the administering apparatus, for example in an external data communication instrument, for the subsequent determination of the filling level.

After measuring and determining the individual capacitance measurement values $C_1$, $C_2$, $C_3$, the sum $C_{sum}$ thereof is established and compared to the individual sums $C_{sum}$ stored in the calibration memory. The pair of electrodes whose associated sum $C_{sum}$ corresponds best to the sum of the established capacitance measurement values $C_1$, $C_2$, $C_3$ is selected. The filling level assigned to the best corresponding sum $C_{sum}$ in each case is considered to be the filling level F of the container 1; the computer unit 6 keeps this filling level F available at the output thereof and outputs the filling level F via an antenna 62 upon request, as described above, or independently without such a request, to an external data communication instrument.

Apparently on account of complex capacitive coupling phenomena of the measuring electrodes 21-26 among themselves, practice also shows strongly deviating curves of the measured capacitances $C_1$, $C_2$, $C_3$ depending on the filling level F, which deviate clearly from the theoretically expected curves depicted in FIG. 17. However, the measurable curve profiles are very well reproducible and exhibit different gradients in different curve portions or filling level regions for each capacitance $C_1$, $C_2$, $C_3$, wherein, counter to theoretical expectations, the greatest gradient of the curve profile or the greatest change in capacitance does not necessarily occur between those measuring electrodes 21-26 between which the fluid level is currently situated. However, since a greater curve gradient means a better measurement resolution/measurement accuracy, it is possible, for the purposes of calculating the filling level, to use a weighted sum as an alternative to the formation of a simple sum of the three individual capacitance measurement values, wherein a dedicated weight is established separately within the scope of the calibration for each of the three summands in each curve portion.

A calibration, in which the container 1 filled with the medicament or a reference container of the same design is emptied, is carried out to obtain a conversion between individual capacitances $C_1$, $C_2$, $C_3$ and a filling level F. During the emptying, the filling level F and the individual capacitances $C_1$, $C_2$, $C_3$ are established in each case. Hence, individual capacitance values $C_1$, $C_2$, $C_3$ are respectively available for each one of the filling levels F assumed during emptying. In the present exemplary embodiment, 30 equidistant filling levels F are assumed during emptying, with the initial state being denoted by 1 and the completely emptied state being denoted by 0. The capacitance values $C_1$, $C_2$, $C_3$ are stored in a reference vector $V_{ref}$ in each case, said reference vector being assigned to the respective filling level F and the respective weights a, b, c. Hence, a reference vector $V_{ref}$ is available for each filling level F. The weights are set by optimization in such a way that the weighted sum $a \cdot C_1 + b \cdot C_2 + c \cdot C_3$ represents a linear approximation to the filling level F.

If the actual filling level F is now intended to be determined on the basis of capacitance values $C_1$, $C_2$, $C_3$ established by measurement, this can be undertaken on the basis of the weights established during the calibration, wherein there are in each case so many weights available for each measurement as capacitance values $C_1$, $C_2$, $C_3$ were established. Initially, a vector $V_{mess}$ [$C_1$, $C_2$, $C_3$] is produced on the basis of the established or measured capacitance values $C_1$, $C_2$, $C_3$, said vector having the capacitance values $C_1$, $C_2$, $C_3$ as components. Subsequently, the vector $V_{mess}$ is compared to the established reference vectors $V_{ref}$ and the reference vector which has the smallest distance from the vector $V_{mess}$ is sought after. In the present exemplary embodiment, the Euclidean distance is used as distance measure. Next, those reference vectors $V_{ref}$ which respectively have the next smallest distance from the vector $V_{mess}$ are established. An interpolating function, for example a linear interpolation function, is determined which, when applied to the reference vectors $V_{ref}$ established by calibration, supplies the filling level F assigned to these back in each case. The capacitance values $C_1$, $C_2$, $C_3$ are inserted into the interpolation function and an averaged filling level value is obtained.

Figure 16:
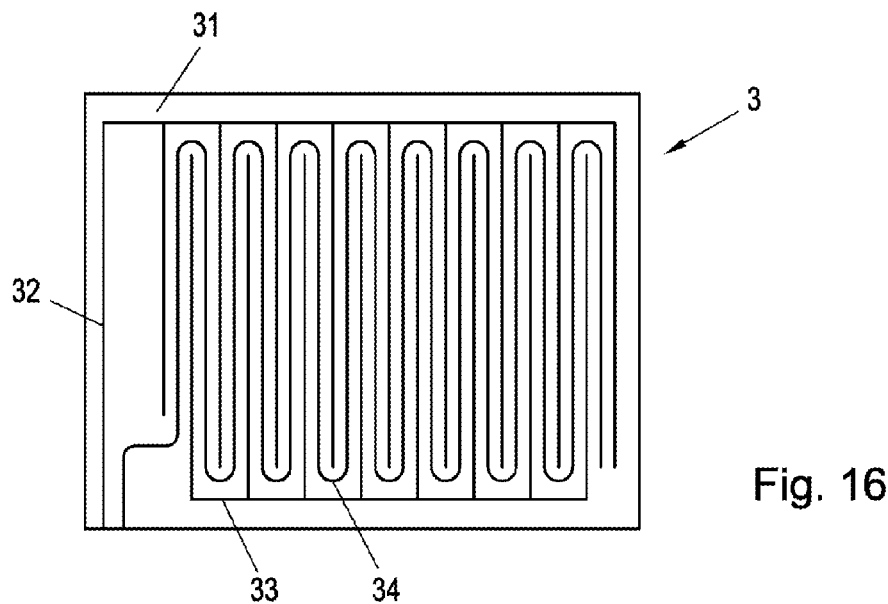
FIG. 16 shows shielding in the form of a film with conductors arranged thereon.

For reasons of space, the antenna 62 may advantageously be arranged outside on the shielding 3. In order to ensure an advantageous combination, the shielding 3 has a film 31 made of an electrically and magnetically nonconductive material, such as e.g. plastic. Conductors 32-34 in the form of conductor tracks are applied to the film 31, which is depicted in FIG. 16. When the conductors 32-34 are embodied on the film 31 in such a way that there are no large-area closed conductor loops, in which eddy currents can form, the magnetic fields emitted by the external data communication instrument are not significantly influenced by the shielding 3 and may be received by the antenna 62. Furthermore, this also makes it possible to transfer energy to the antenna 62 in the form of electromagnetic waves, said energy being sufficient to supply electrical components connected to the antenna with energy to a sufficient extent.

To the extent that additional accuracy is required when determining the filling level F in the interior of the container 1, provision can be made for a measurement value for the filling level F to then be invalidated or declared invalid if the electric field in the outer region of the container 1 was falsified, for example by the contact, or approach, of electrically conductive bodies or of bodies with a high dielectric permittivity.

The shielding 3 has an electrically and magnetically nonconductive film 31, on which a multiplicity of conductors 32, 33, 34 are formed by coating. In the present exemplary embodiment, the film 31 consists of a flexible plastic. The conductor tracks have a layer thickness of approximately 50 μm and a width of approximately 1000 μm. Widths of the conductors 32-34 of between 100 μm and 3000 μm are advantageous.

In order to avoid the formation of eddy currents and, as a result thereof, an impairment of a communication based on inductive coupling, in particular NFC communication, the width of the conductors 32-34 can be restricted to less than 3 mm. Moreover, as depicted in FIG. 16, the conductors 32-34 may be embodied to be free from loops, i.e. free from closed conductor loops, i.e. not comprise any closed loops, in order to prevent the formation of eddy currents to a sufficient extent and avoid an impairment of an NFC communication but, at the same time, also avoid capacitive influence on the measuring electrodes 21-26 situated within the shielding 3.

Hence, two of the three conductors 32, 33 are embodied as meshing comb conductors 32, 33 and the third conductor 34 extends in a meandering fashion between the two comb conductors 32, 33 in this special exemplary embodiment of the invention. Naturally, in addition to this exemplary embodiment, there are also a multiplicity of further exemplary embodiments of the loop-free arrangement of a plurality of conductor tracks or electrodes, which are not electrically connected to one another, on the surface of a film 31 or in the interior of a film, or between individual plies of a film built up from a number of plies. Moreover, conductors 32-34 may be printed on both the front side and the rear side of the film 31. Alternatively, it is also possible for a plurality of meandering conductors 34 to be arranged next to one another between the comb conductors 32, 33 or for a plurality of conductors 34 to be arranged on the film 31 in a spiral fashion.

Figure 18:
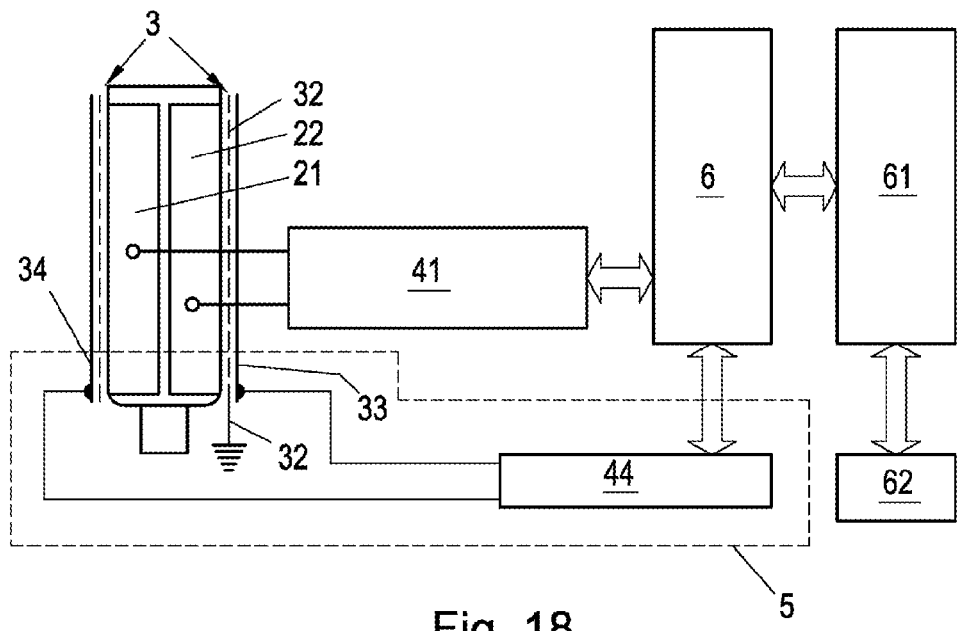
FIGS. 18 and 19 show the embodiments depicted in FIGS. 14 and 15 with the additional provision of a contact detection.
Figure 19:
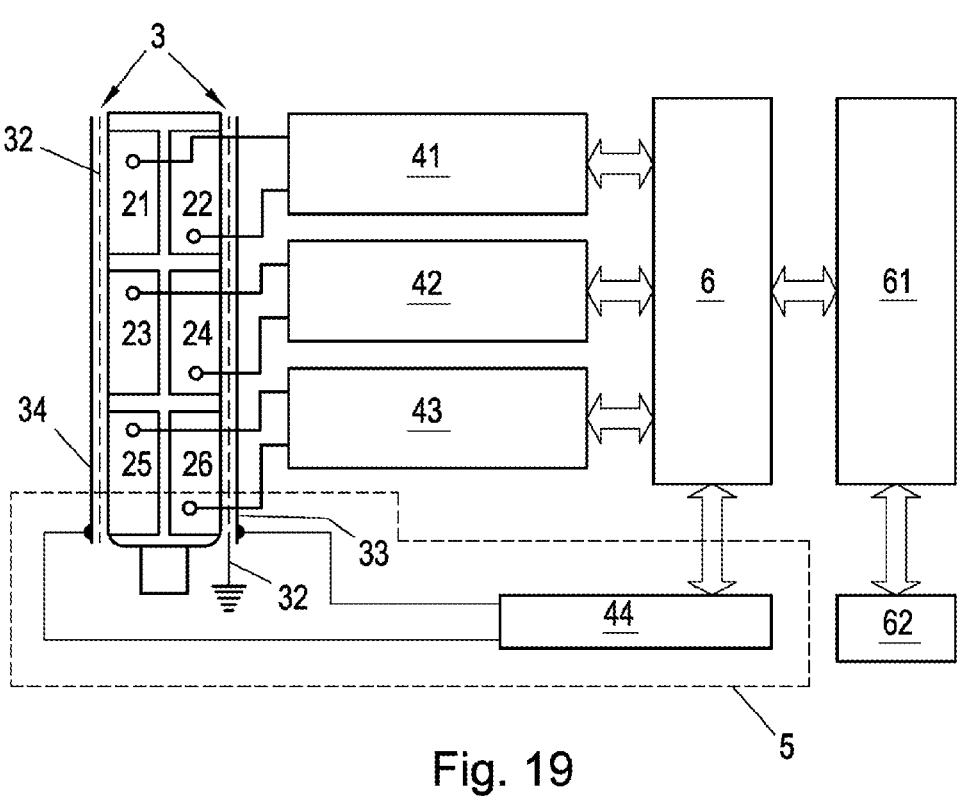
Figure 22A:
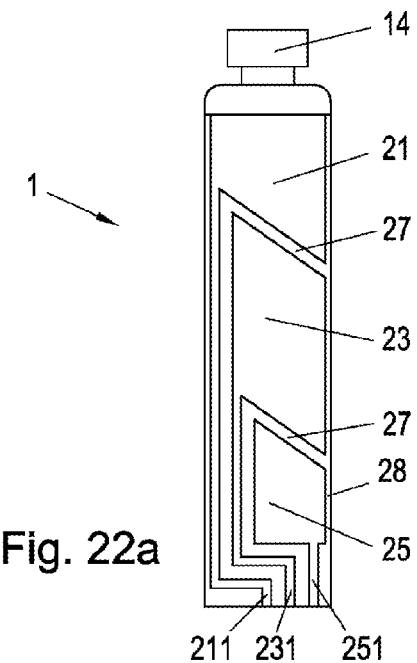
FIG. 22 shows a further embodiment of a container, corresponding to the FIGS. 10a-d, with obliquely extending electrodes.
Figure 22B:
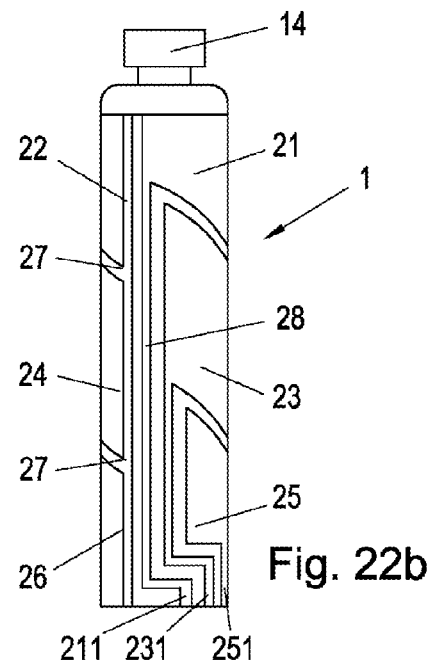
Figure 22C:
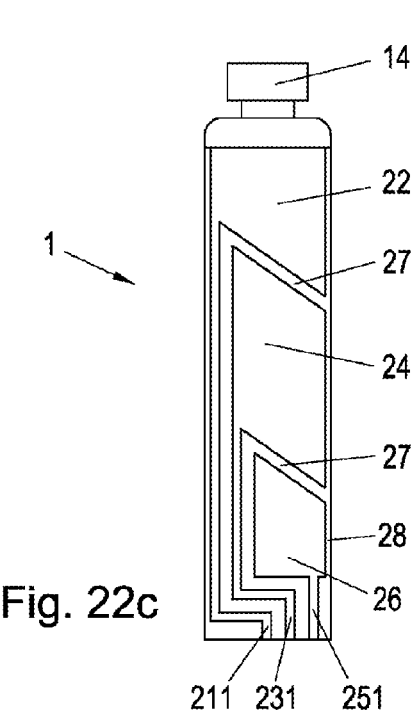
Figure 22D:
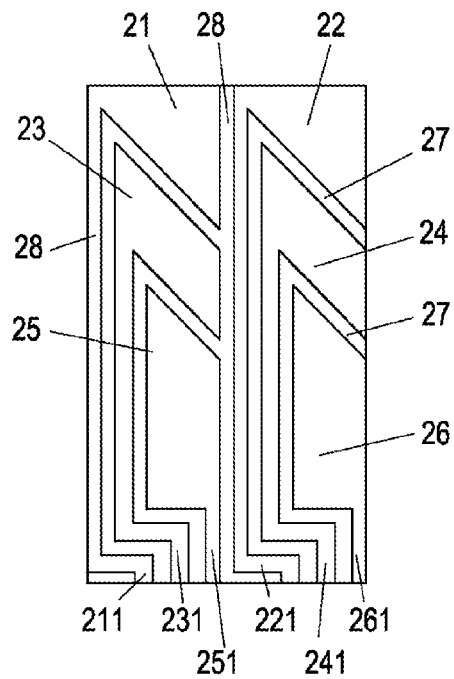

Two conductor tracks, that is to say one of the two comb conductors 33 and the meandering conductor 34, are used as a contact sensor 5. The second comb conductor 32 is connected to a predetermined ground potential and serves as electrical shielding. If a person touches the shielding 3 or if the person comes close to the shielding 3, there is a change in the capacitance between the conductors 33, 34 of the contact sensor 5 as a result of the change in the permittivity of the surroundings. The change in this capacitance between the conductors 33, 34 can be determined by means of a further capacitance measuring device 44; the conductors 33, 34 of the shielding 3 or the contact sensor 5 are connected to the measuring connectors of the further capacitance measuring device 44. This further capacitance measuring device 44 determines a further capacitance value C' and forwards the latter, as depicted in FIG. 18 and FIG. 19, to the computer unit 6. If the change in the established further capacitance measurement value C' exceeds a predetermined threshold T, the assumption is made that the filling level F established on the basis of the capacitance measurement values $C_1$, $C_2$, $C_3$ is erroneous due to the contact. The established filling level F is invalidated.

In the present special exemplary embodiment of the invention, use is made of shielding 3 which, at the same time, acts as a contact detection 5 and consists of the comb conductor 32 and the meandering conductor 34. However, from a physical or functional view, electrical shielding 3 and contact detection 5 are two completely separate and different units which can be realized by the specific arrangement depicted in FIG. 16 in a particularly advantageous manner, namely producible in one plane by printing. Naturally, this functional separation of electrical shielding 3 and contact detection 5 is readily possible. It is only for reasons of simpler illustration that the conductors 32, 33, 34 of the shielding 3 or of the contact detection 5, which lie in a plane of the film 31, were illustrated next to one another in FIGS. 14, 15, 18 and 19.

An alternative embodiment of the invention facilitates the removal of the container 1 from the administering apparatus 100 in the case of a replacement. A carrier (not depicted here) is arranged outside of the container 1 between the container 1 and the shielding 3. Measuring electrodes 21-26 are situated thereon. The carrier abuts against the container 1 and is advantageously formed by part of the housing of the administering apparatus 100. The measuring electrodes 21-26 are arranged on the wall of the carrier abutting against the container 1. The housing of the administering apparatus 100 can be opened and the container 1 can be removed from the housing of the administering apparatus 100. The carrier forms a part of the administering apparatus 100.

Advantageously, the communication controller 61, the computer unit 6, the capacitance measuring devices 41-44 and the antenna 62 may be arranged on the film 31.

A further preferred embodiment of the invention, which is depicted in FIG. 20, shows an administering apparatus with a cover cap 9. This embodiment substantially corresponds to the embodiment depicted above, with the following only illustrating the differences from the embodiment above in more detail.

The cover cap 9 is detachably connected to the carrier body 200 of the administering apparatus by means of one or more latching elements 109. The cover cap 9 surrounds, in a sheath-like manner, the container 1 and the measuring electrodes 21-26 arranged on the container 1. In contrast to the embodiment above, the shielding 3 and the contact sensor 5 are arranged in the body of the cover cap 9. To the extent that the cover cap 9 is placed onto the carrier body 200, the measuring electrodes 21-26 are shielded by the shielding 3. The shielding 3 is cast into the body of the cover cap 9 in the present embodiment and surrounded by the latter on all sides. Like in the present embodiment as well, the shielding 3 is arranged on a film which is surrounded or enclosed on all sides by the cover cap 9. In the present case, the shielding 3 surrounds the measuring electrodes 21-26 in the end region of the cover cap 9 which faces the injection needle 103. Alternatively, it is also possible for the film and/or the shielding 3 to be arranged on the outside on the cover cap 9.

The cover cap 9 has a recess 99 as a passage for the injection needle 103 in this end region. Alternatively, it is also possible for the injection needle 103 to be completely surrounded by the housing of the cover cap 9.

In a second alternative, the cover cap 9 is embodied in the form of a sleeve which is open at the end of the injection needle 103. As a result, injecting or administering the liquid is possible even when the cover cap is put on. Therefore, overall, it is not necessary for the cover cap to cover the injection needle 103 or the container 1 from all sides.

In order to facilitate a view of the viewing openings 108 in the carrier body 200 of the administering apparatus, the cap 9 respectively has further viewing openings 98 at the position in front of the viewing openings.

FIG. 21 shows the administering apparatus 100 from the outside. In this illustration, it is also possible to see a display unit 90, which is connected to the computer unit 6 (FIGS. 23 and 25) and actuated by the latter. The connection lines of the display unit 90 extend outside of the shielding 3 within the interior of the cover cap 9.

FIGS. 22*a*-*d* show a possible configuration of the electrodes 21-26. The individual measuring electrodes 21-26 are guided by way of electrically conductive connections with connection contacts 211, 221, 231, 241, 251, 261. Advantageously, just like the measuring electrodes 21-26 and the connection contacts 211, 221, 231, 241, 251, 261, these connections are arranged inside or outside on the container 1 as conductor layers.

In principle, it is possible here to use all of the electrode forms depicted in FIGS. 9*a* to 12*d*, with the respective measuring electrodes 21-26 being guided to the container-side connection contacts 211, 221, 231, 241, 251, 261 by way of, in each case, a line assigned to the electrode 21-26 and extending in the outer region of the container 1. To the extent that only two measuring electrodes are used, as depicted in FIGS. 9*a*-*d*, only two connection contacts 211, 221 are present as well.

Figure 23:
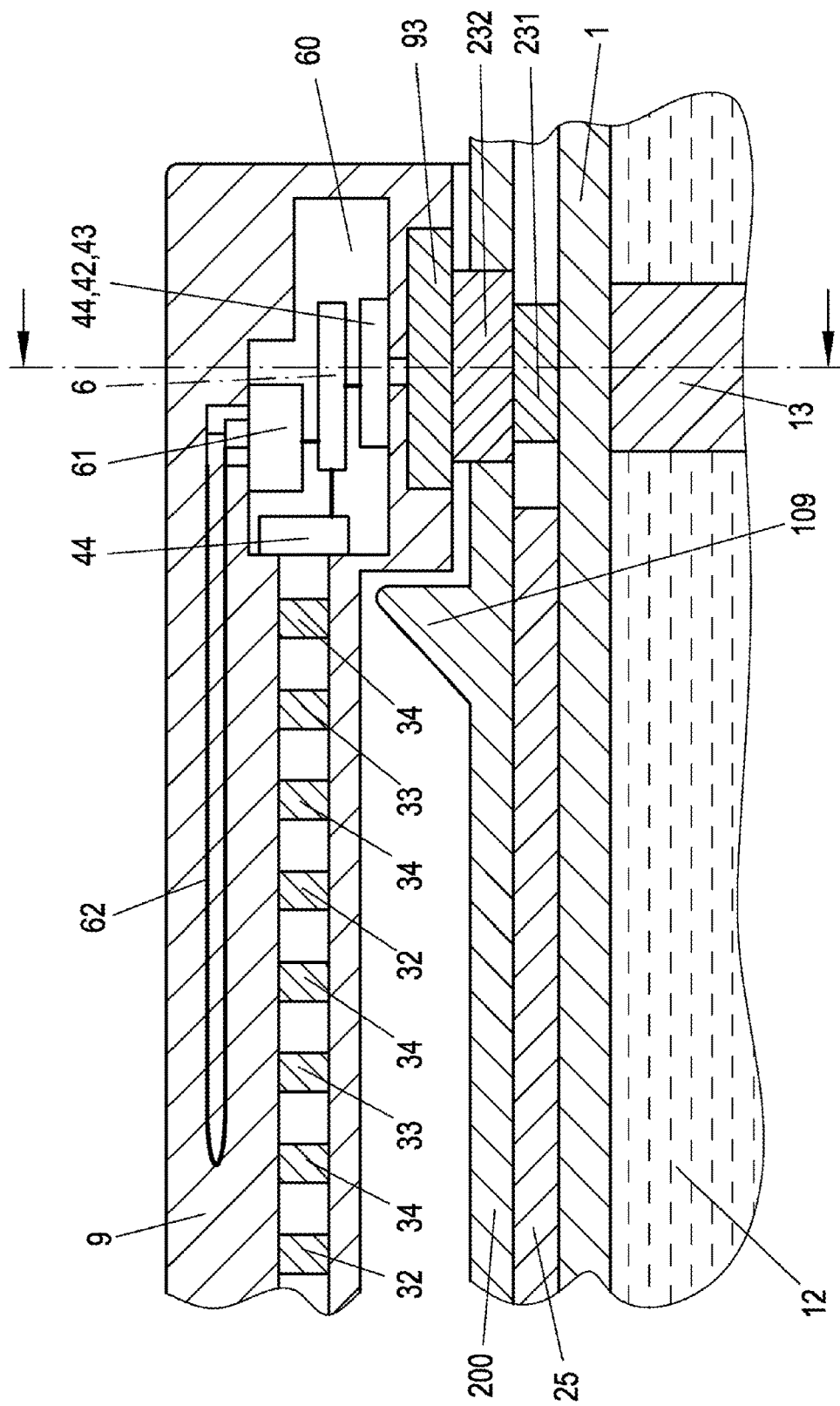
FIG. 23 shows a detail from FIG. 20.

FIG. 23 shows a sectional illustration along the section B-B from FIG. 20 and. The carrier body 200 of the administering apparatus 100 respectively has a through-contact 212, 222, 232, 242, 252, 262 for each one of the connection contacts 211, 221, 231, 241, 251, 261, which through-contact is guided to the outer surface of the carrier body 200 and arranged in a manner such that it is able to be tapped from the outside and able to be electrically contacted.

Figure 25:
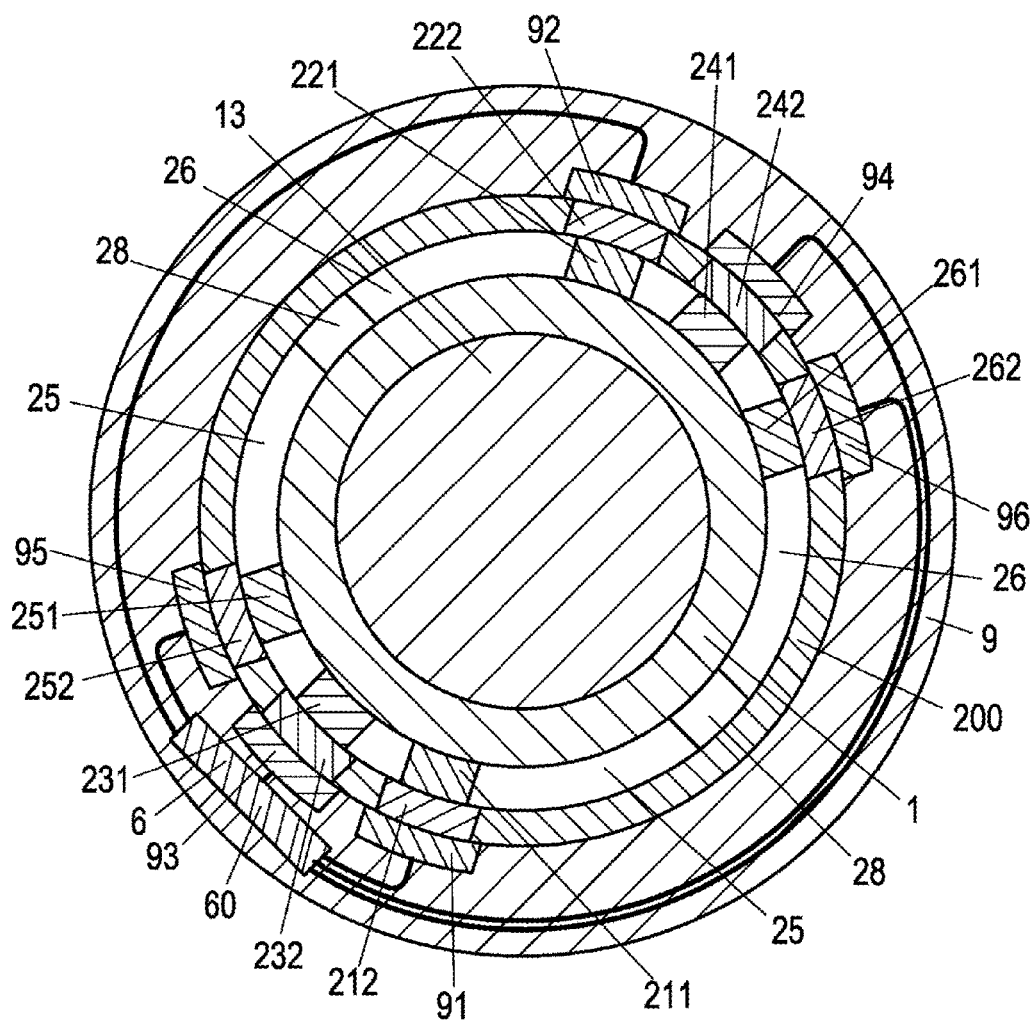

As can also be seen from FIG. 25, the cover cap 9 has, at its open end region facing the carrier body 200, a number of connection contacts 91, 92, 93, 94, 95, 96, which are connectable to the through-contacts 212, 222, 232, 242, 252, 262 in an electrically conductive manner. In order to avoid mistakes, the latch elements 109 may have such an embodiment that latching is only possible in a single position, in which each of the through-contacts 212, 222, 232, 242, 252, 262 also respectively contacts one of the connection contacts 91, 92, 93, 94, 95, 96 of the cover cap 9. All connection contacts 211, 221, 231, 241, 251, 261 and through-contacts 212, 222, 232, 242, 252, 262, and connection contacts 91, 92, 93, 94, 95, 96 of the cover cap 9 are made from electrically conductive material, in particular from copper.

Each one of the connection contacts 91, 92, 93, 94, 95, 96 is respectively connected to a connector of a capacitance measuring unit 41, 42, 43, and so the respective capacitance measuring unit 41, 42, 43 in each case establishes the capacitance between in each case two measuring electrodes 21, 22; 23, 24; 25, 26 arranged opposite one another. The capacitance measuring units 41, 42, 43 are connected to the computer unit 6.

The antenna 62 depicted in FIG. 23 is arranged in the outer region of the shielding 3, on or in the cap 9. In the present exemplary embodiment, the antenna 62, and the shielding 3 as well, is cast with the cap 9 and completely surrounded by the body of the cap 9. The antenna 9 is preferably arranged on a film which is arranged outside of the film of the shielding 3, with both films being completely surrounded by the body of the cap.

The antenna 62 is connected to a communication controller which is connected to the computer unit 6. Two of the three conductors 32, 33, 34 of the shielding 3 are connected in an electrically conductive manner to the further capacitance measuring device 44, which is connected to the computer unit 6.

The capacitance measuring devices 41, 42, 43, the further capacitance measuring device 44, the communication controller 61 and, optionally, a further battery (not depicted in the figures) are integrated in a common housing 60, which is arranged in the interior of the cover cap 9, preferably cast with the latter.

Figure 24:
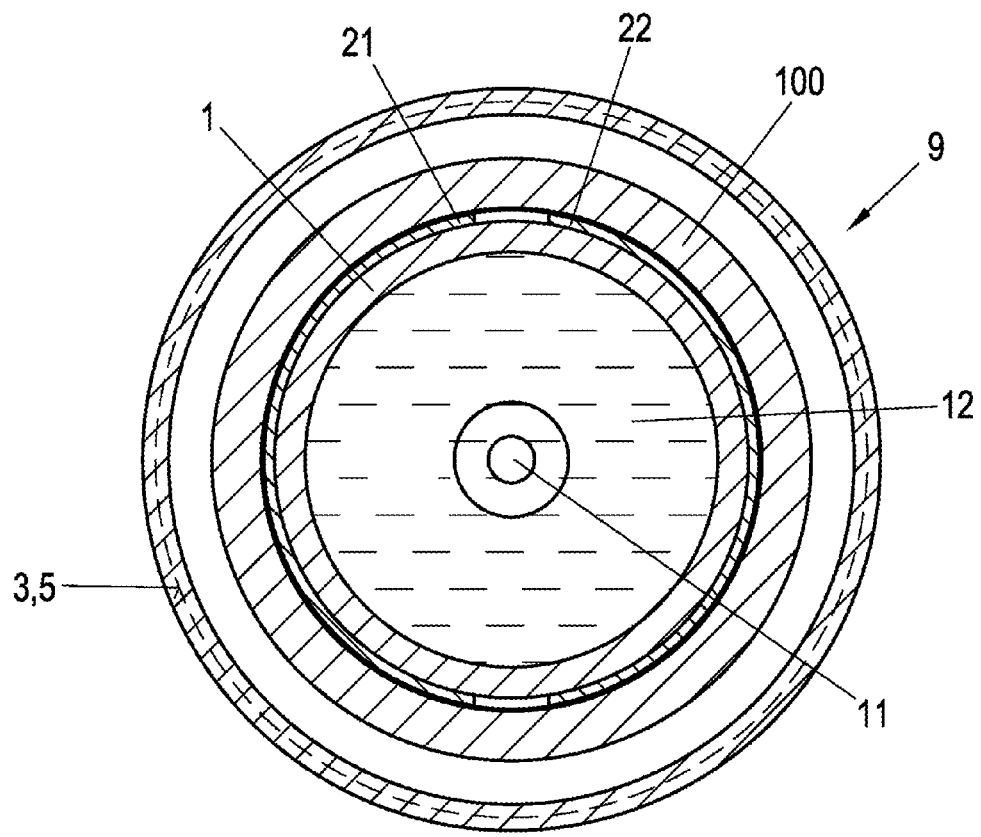
FIGS. 24 and 25 show sections through the embodiment of the invention depicted in FIG. 20.

FIG. 24 shows a section C-C, which is normal to the direction of advance, in the end region of the container 1. It is possible to identify here that the shielding 3 arranged in the cap 9 surrounds the measuring electrodes 21-26. Otherwise, reference is made to the description of FIG. 13.

Figure 26:
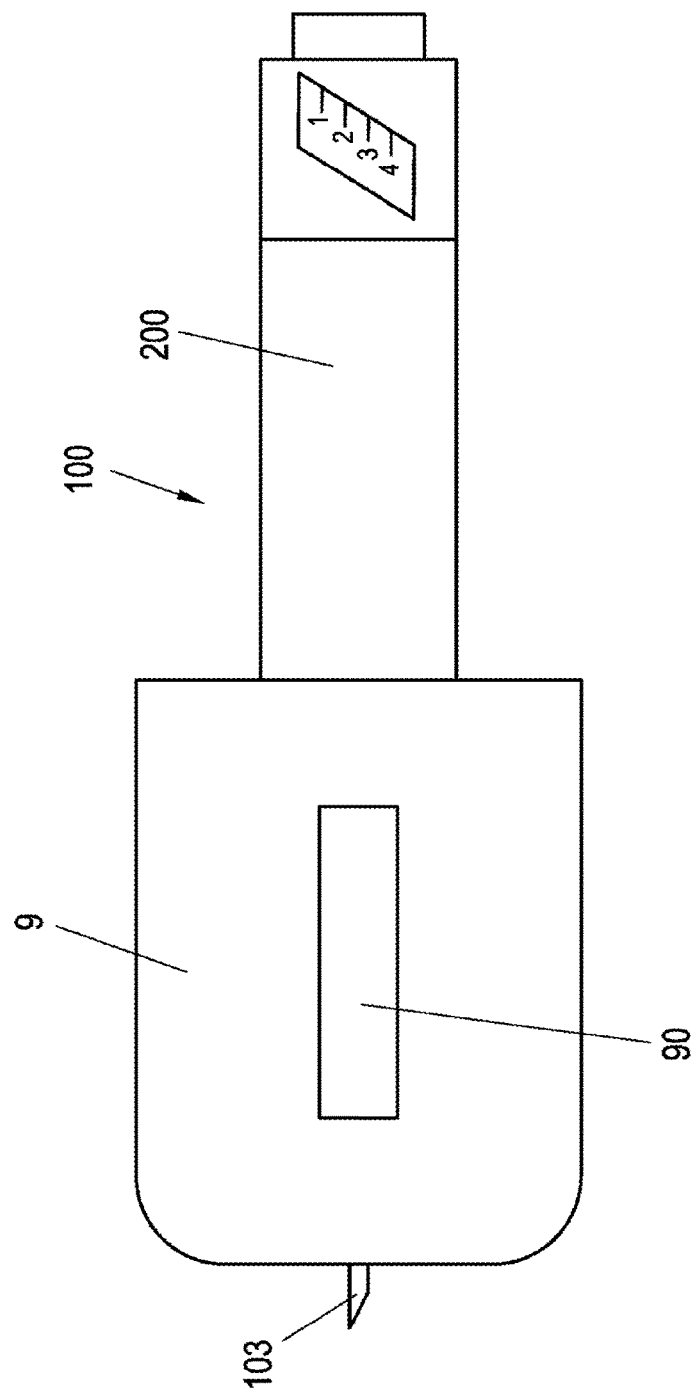
FIG. 26 shows a further embodiment of the invention which makes do without shielding.

FIG. 26 shows a further embodiment of the invention which, however, dispenses with shielding 3. In order nevertheless to ensure an accurate measurement, provision is made for an enlarged the cover cap 9, which prevents access closer than 10 mm to the measuring electrodes 21-26. In this embodiment, no further capacitance measuring device is provided either on account of the lack of shielding.

The invention claimed is:

1. An administering apparatus provided for administering liquids or liquid medicaments to persons and having a reusable filling level measuring system, the administering apparatus comprising:
   a container to be filled with the liquid, said container having an end with an opening for administering the liquid and said container having an outer region;
   at least one pair of capacitive measuring electrodes disposed opposite one another in said outer region of said container for determining a filling level of the liquid in said container;
   electrical shielding surrounding said at least one pair of capacitive measuring electrodes and said container as a sheath, said electrical shielding being formed of conductor tracks applied to a film, and said electrical shielding being disposed at a radial distance from said at least one pair of capacitive measuring electrodes;
   a communication controller applied to said film;
   at least one capacitance measuring device applied to said film for establishing a capacitance between said at least one pair of capacitive measuring electrodes;
   a computer unit applied to said film;
   an antenna applied to said film for transferring measurement values established by said at least one pair of capacitive measuring electrodes or values derived from the measurement values;
   a cover cap surrounding said at least one pair of capacitive measuring electrodes and said container as a sheath, said cover cap being coupled to the administering apparatus by a detachable connection, and said cover cap having a plurality of electrical contacts each being electrically conductively connected to a respective one of said at least one pair of capacitive measuring electrodes; and
   said film with said electrical shielding, said capacitance measuring device, said computer unit and said antenna being integrated in said cover cap.

2. The administering apparatus according to claim 1, wherein said container has a wall, and said at least one pair of capacitive measuring electrodes abuts against said wall.

3. The administering apparatus according to claim 1, wherein the values are filling level values.

4. The administering apparatus according to claim 1, wherein said conductor tracks have at least one of:
   conductors formed without loops; or
   conductors formed with free from closed conductor loops; or
   conductors having a thickness of at most 3 mm.

5. The administering apparatus according to claim 4, which further comprises:
   a computer unit having an output;
   said capacitance measuring device establishing a capacitance value being fed to said computer unit; and
   said computer unit determining the filling level of the liquid in said container based on the established capacitance value by using a predetermined stored calibration function and keeping the filling level available at said output of said computer unit.

6. The administering apparatus according to claim 5, which further comprises:
   a further capacitance measuring device; and
   a contact sensor disposed outside of or in a vicinity of said shielding, said contact sensor having sensor electrodes connected to said capacitance further measuring device.

7. The administering apparatus according to claim 6, wherein:
   said further capacitance measuring device establishes a further capacitance value being fed to said computer unit; and
   said computer unit suppresses, or characterizes as invalid, a forwarding of the filling level established by said computer unit if the established further capacitance value exceeds a predetermined threshold.

8. The administering apparatus according to claim 6, which further comprises a battery disposed in said cover cap, said battery being connected to and supplying electrical energy to said at least one capacitance measuring device, said further capacitance measuring device, said computer unit and said communication controller.

9. The administering apparatus according to claim 5, which further comprises a multiplicity of pairs of additional measuring electrodes disposed at said container.

10. The administering apparatus according to claim 9, which further comprises additional capacitance measuring devices each being disposed downstream of a respective pair of said measuring electrodes on each respective pair of additional measuring electrodes, said capacitance measuring devices outputting established capacitance values to said computer unit.

11. The administering apparatus according to claim 1, wherein said conductors have a thickness of between 50 μm and 150 μm.

12. The administering apparatus according to claim 1, wherein said conductor tracks include first, second and third separate conductors disposed on said film, said first conductor and said second conductor are constructed as meshing comb conductors and said third conductor has a meandering form and lies between said comb conductors.

13. The administering apparatus according to claim 12, which further comprises a capacitance measuring device, said at least one pair of capacitive measuring electrodes including two opposite measuring electrodes connected to said capacitance measuring device.

14. The administering apparatus according to claim 13, wherein said capacitance measuring device has a ground connector, and one of said conductors constructed as a comb conductor is connected to said ground connector of said capacitance measuring device.

15. The administering apparatus according to claim 14, wherein said second conductor is connected to said ground connector of said capacitance measuring device.

16. The administering apparatus according to claim 12, which further comprises a contact sensor, said contact sensor including said shielding or said contact sensor being disposed outside of or in a vicinity of said shielding.

17. The administering apparatus according to claim 16, wherein said contact sensor is a capacitive contact sensor, and said contact sensor includes said first comb conductor and said meandering conductor of said shielding as sensor electrodes.

18. The administering apparatus according to claim 1, wherein said at least one pair of capacitive measuring electrodes are assigned to one another in pairs and lie opposite one another in a circumferential direction of said container.

19. The administering apparatus according to claim 18, which further comprises a plunger disposed in said container and pushing the liquid towards said opening in a direction of advance for administering the liquid, said capacitive measuring electrodes lying diametrically opposite one another and lying at an equivalent level in said direction of advance of said plunger.

20. The administering apparatus according to claim 1, wherein said cover cap has a continuous recess formed therein for administering the liquid through said cover cap in a vicinity of said opening of said container.

* * * * *